US008404672B2

(12) United States Patent  (10) Patent No.: US 8,404,672 B2
Pitts et al.  (45) Date of Patent: Mar. 26, 2013

(54) SUBSTITUTED HETEROCYCLIC COMPOUNDS

(75) Inventors: William J. Pitts, Newtown, PA (US); Alaric J. Dyckman, Lawrenceville, NJ (US); Steven H. Spergel, Warrington, PA (US); Scott Hunter Watterson, Pennington, NJ (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 68 days.

(21) Appl. No.: 13/145,721

(22) PCT Filed: Jan. 22, 2010

(86) PCT No.: PCT/US2010/021694
§ 371 (c)(1),
(2), (4) Date: Jul. 21, 2011

(87) PCT Pub. No.: WO2010/085582
PCT Pub. Date: Jul. 29, 2010

(65) Prior Publication Data
US 2012/0022041 A1  Jan. 26, 2012

Related U.S. Application Data

(60) Provisional application No. 61/146,837, filed on Jan. 23, 2009.

(51) Int. Cl.
*A61K 31/4402* (2006.01)
*C07D 413/14* (2006.01)
(52) U.S. Cl. .................. 514/210.18; 546/269.1
(58) Field of Classification Search .......... None
See application file for complete search history.

(56) References Cited

U.S. PATENT DOCUMENTS

| | | | |
|---|---|---|---|
| 7,199,142 B2 | 4/2007 | Chen | |
| 7,220,734 B2 | 5/2007 | Doherty | |
| 7,309,721 B2 | 12/2007 | Budhu | |
| 2005/0033055 A1 | 2/2005 | Bugianesi et al. | |
| 2005/0070506 A1 | 3/2005 | Doherty et al. | |
| 2006/0173000 A1 | 8/2006 | Kesteleyn et al. | |
| 2007/0203100 A1 | 8/2007 | Pan et al. | |
| 2008/0200535 A1 | 8/2008 | Ohmori et al. | |
| 2008/0249093 A1 | 10/2008 | Colandrea et al. | |
| 2008/0280876 A1 | 11/2008 | Hobson et al. | |
| 2010/0160369 A1 | 6/2010 | Canne et al. | |

FOREIGN PATENT DOCUMENTS

| | | |
|---|---|---|
| WO | WO 03/062248 | 7/2003 |
| WO | WO 03/062252 | 7/2003 |
| WO | WO 03/105771 | 12/2003 |
| WO | WO 2004/046143 | 6/2004 |
| WO | WO 2005/000833 | 1/2005 |
| WO | WO 2006/047195 | 5/2006 |
| WO | WO 2006/088944 | 8/2006 |
| WO | WO 2006/100631 | 9/2006 |
| WO | WO 2006/100633 | 9/2006 |
| WO | WO 2006/115188 | 11/2006 |
| WO | WO 2006/131336 | 12/2006 |
| WO | WO 2007/024922 | 3/2007 |
| WO | WO 2007/061458 | 5/2007 |
| WO | WO 2007/085451 | 8/2007 |
| WO | WO 2007/109334 | 9/2007 |
| WO | WO 2007/116866 | 10/2007 |
| WO | WO 2008/029306 | 3/2008 |
| WO | WO 2008/029371 | 3/2008 |
| WO | WO 2008/035239 | 3/2008 |
| WO | WO 2008/074820 | 6/2008 |
| WO | WO 2008/079382 | 7/2008 |
| WO | WO 2008/141731 | 11/2008 |
| WO | WO 2009/011850 | 1/2009 |
| WO | WO 2009/043889 | 4/2009 |
| WO | WO 2009/043890 | 4/2009 |
| WO | WO 2009/057079 | 5/2009 |
| WO | WO 2009/131090 | 10/2009 |
| WO | WO 2009/151529 | 12/2009 |
| WO | WO 2010/039237 | 4/2010 |
| WO | WO 2010/039238 | 4/2010 |
| WO | WO 2010/085581 | 7/2010 |
| WO | WO 2010/085584 | 7/2010 |

OTHER PUBLICATIONS

U.S. Appl. No. 13/145,730, (corresponding to WO 2010/085581), filed Jul. 21, 2011, Scott H. Watterson.

(Continued)

*Primary Examiner* — Zinna Northington Davis
(74) *Attorney, Agent, or Firm* — Gary D. Greenblatt

(57) ABSTRACT

Disclosed are compounds of Formula (I)

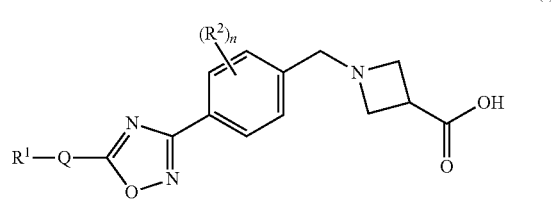

or pharmaceutically acceptable salts thereof, wherein Q is

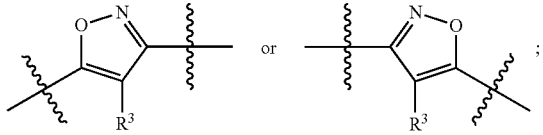

$R^1$ is cycloalkyl, heteroaryl, or heterocyclyl, each optionally substituted with one to five substituents independently selected from $C_1$ to $C_6$ alkyl, $C_1$ to $C_4$ haloalkyl, $-OR^4$, and/or halogen; and $R^2$, $R^3$, $R^4$, and n are defined herein. Also disclosed are methods of using such compounds as selective agonists for G protein-coupled receptor $S1P_1$, and pharmaceutical compositions comprising such compounds. These compounds are useful in treating, preventing, or slowing the progression of diseases or disorders in a variety of therapeutic areas, such as vascular disease and autoimmune diseases.

12 Claims, No Drawings

OTHER PUBLICATIONS

U.S. Appl. No. 13/145,728, (corresponding to WO 2010/085584), filed Jul. 21, 2011, Alaric J. Dyckman.
IPER/Search report for PCT/US2010/021694 issued Jul. 26, 2011.
Anliker et al., J. Biol. Chem., 279:20555 (2004).
Brinkman et al., Am. J. Transplant., 4:1019 (2004).
Brinkman et al., J. Biol. Chem., 277:21453 (2002).
Kenji Chiba, Pharmacology & Therapeutics, 108:308 (2005).
Fujino et al., J. Pharmacol. and Exp. Ther., 305:70 (2003).
Hale et al., J. Med. Chem. 47:6662 (2004).
Hale et al., Bioorg. Med. Chem. Lett., 14:3501 (2004).
Kahan et al., Transplantation, 76:1079 (2003).
Kappos et al., N. Engl. J. Med., 355:1124 (2006).
Koyrakh et al., Am. J. Transplant., 5:529 (2005).
Forrest et al., J. Pharmacol. Exp. Ther., 309:758 (2004).
Mandala et al., Science, 296:346 (2002).
Morris et al., Eur. J. Immunol., 35:3570 (2005).
Sanna et al., J. Biol. Chem., 279:13839 (2004).
Webb et al., J. Neuroimmunol., 153:108 (2004).

SUBSTITUTED HETEROCYCLIC COMPOUNDS

This application is a 371 of PCT/US2010/021694 filed Jan. 22, 2010 which claims benefit of 61/146,837 filed Jan. 23, 2009.

The present invention generally relates to heterocyclic compounds useful as $S1P_1$ agonists. Provided herein are heterocyclic compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Down-regulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant.*, 4:1019 (2004); Webb et al., *J. Neuroimmunol.*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N. Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., *N. Engl. J. Med.*, 335:1124 (2006)). The observed bradycardia is commonly thought to be due to agonism at the $S1P_3$ receptor. This conclusion is based on a number of cell based and animal experiments. These include the use of $S1P_3$ knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)).

The following applications have described compounds as $S1P_1$ agonists: WO 03/061567 (U.S. Publication No. 2005/0070506), WO 03/062248 (U.S. Pat. No. 7,351,725), WO 03/062252 (U.S. Publication No. 2005/0033055), WO 03/073986 (U.S. Pat. No. 7,309,721), WO 03/105771, WO 05/058848, WO 06/047195, WO 06/100633, WO 06/115188, WO 06/131336, WO 2007/024922, WO 07/116,866, WO 08/023,783 (U.S. Publication No. 2008/0200535), and WO 08/074,820. Also see Hale et al., *J. Med. Chem.*, 47:6662 (2004).

There still remains a need for compounds useful as $S1P_1$ agonists and yet having selectivity over $S1P_3$.

Applicants have found potent compounds that have activity as $S1P_1$ agonists. Further, applicants have found compounds that have activity as $S1P_1$ agonists and are selective over $S1P_3$. These compounds are provided to be useful as pharmaceuticals with desirable stability, bioavailability, therapeutic index, and toxicity values that are important to their drugability.

SUMMARY OF THE INVENTION

The present invention fills the foregoing need by providing compounds of Formula (I):

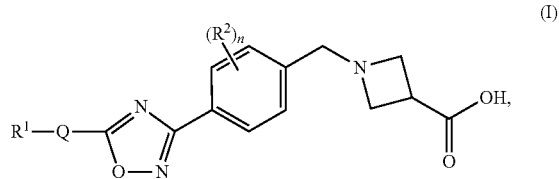

or pharmaceutically acceptable salts thereof, wherein:
Q is

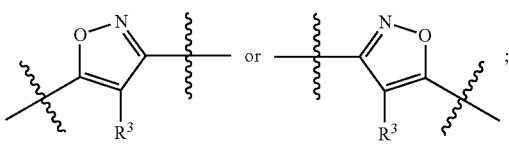

n is zero or an integer selected from 1 through 4;
$R^1$ is cycloalkyl, heteroaryl, or heterocyclyl, each optionally substituted with one to five substituents independently selected from $C_1$ to $C_6$ alkyl, $C_1$ to $C_4$ haloalkyl, —$OR^4$, and/or halogen;
each $R^2$ is independently selected from hydrogen, $C_1$ to $C_6$ alkyl, $C_1$ to $C_4$ haloalkyl, —$OR^4$, and/or halogen;
$R^3$ is hydrogen, alkyl, cycloalkyl, haloalkyl, —$C(O)OR^5$, or —$C(O)NR_aR_b$;
each $R^4$ is independently selected from $C_1$ to $C_6$ alkyl, $C_1$ to $C_4$ haloalkyl, and/or benzyl;
$R^5$ is alkyl or benzyl; and
$R_a$ and $R_b$ are independently selected from hydrogen, alkyl, haloalkyl, and/or benzyl.

Also described are pharmaceutical compositions comprising a compound of Formula (I), or a pharmaceutically acceptable salt thereof; and a pharmaceutically acceptable carrier.

Further described is a method of treating a disease or disorder associated with the activity of G protein-coupled receptor $S1P_1$, the method comprising administering to a mammalian patient a compound of Formula (I) or a pharmaceutically acceptable salt thereof.

The compounds of Formula (I) and compositions comprising the compounds are $S1P_1$ agonists, which are selective for $S1P_1$ activity over $S1P_3$ activity. The compounds of Formula (I) and compositions comprising said compounds may be used in treating, preventing or curing various $S1P_1$ receptor-related conditions while reducing or minimizing the side effects due to $S1P_3$ activity. Pharmaceutical compositions comprising these compounds are useful in treating, preventing, or slowing the progression of diseases or disorders in a variety of therapeutic areas, such as autoimmune and vascular diseases.

DETAILED DESCRIPTION

One embodiment provides a compound of Formula (I),

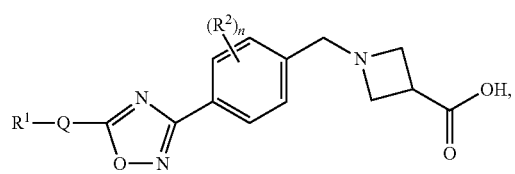

(I)

or a pharmaceutically acceptable salt thereof:
Q is

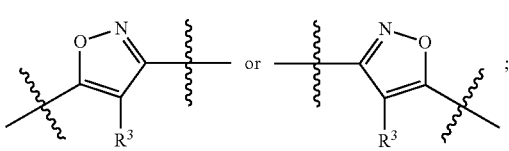

n is zero or an integer selected from 1 through 4; $R^1$ is $C_3$ to $C_8$ cycloalkyl, heteroaryl, or heterocyclyl, each optionally substituted with one to five substituents independently selected from $C_1$ to $C_6$ alkyl, $C_1$ to $C_4$ haloalkyl, —$OR^4$, and/or halogen;
each $R^2$ is independently selected from hydrogen, $C_1$ to $C_6$ alkyl, $C_1$ to $C_4$ haloalkyl, —$OR^4$, and/or halogen;
$R^3$ is hydrogen, $C_1$ to $C_6$ alkyl, $C_3$ to $C_8$ cycloalkyl, $C_1$ to $C_4$ haloalkyl, or —$C(O)OR^5$;
each $R^4$ is independently selected from $C_1$ to $C_6$ alkyl, $C_1$ to $C_4$ haloalkyl, and/or benzyl; and
$R^5$ is $C_1$ to $C_6$ alkyl or benzyl.

One embodiment provides a compound of Formula (I) or a pharmaceutically acceptable salt thereof, wherein:
Q is

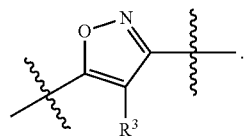

A compound of this embodiment has the structure represented by Formula (Ia):

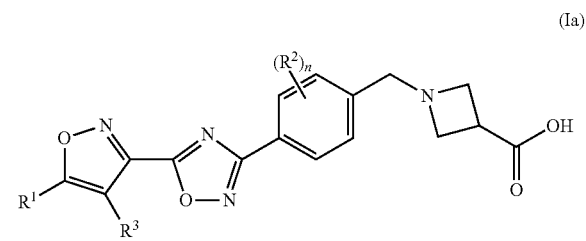

(Ia)

or a pharmaceutically acceptable salt thereof, wherein $R^1$, $R^2$, $R^3$, and n are as defined hereinabove.

One embodiment provides a compound of Formula (I) or a pharmaceutically acceptable salt thereof, wherein:
Q is

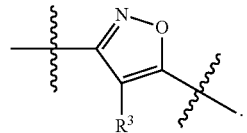

A compound of this embodiment has the structure represented by Formula (Ia):

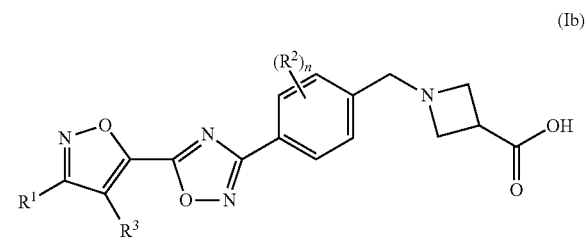

(Ib)

or a pharmaceutically acceptable salt thereof, wherein $R^1$, $R^2$, $R^3$, and n are as defined hereinabove.

One embodiment provides a compound of Formula (I) or a pharmaceutically acceptable salt thereof, wherein n is zero or 1.

One embodiment provides a compound of Formula (I) or a pharmaceutically acceptable salt thereof, wherein n is zero.

One embodiment provides a 2,2,2-trifluoroacetic acid salt of a compound according to Formula (I).

One embodiment provides a compound of Formula (I) or a pharmaceutically acceptable salt thereof, wherein $R^1$ is $C_3$ to $C_8$ cycloalkyl optionally substituted with one to five substituents independently selected from $C_1$ to $C_6$ alkyl, $C_1$ to $C_4$ haloalkyl, —$OR^4$, and/or halogen. Suitable cycloalkyl groups include $C_3$ to $C_6$ cycloalkyl groups. For example, this embodiment provides compounds of Formula (I) wherein $R_1$ is $C_3$ to $C_6$ cycloalkyl and n is zero or 1. Preferably, $R^3$ is $C_1$ to $C_6$ alkyl, $C_3$ to $C_8$ cycloalkyl, $C_1$ to $C_6$ haloalkyl, or —$C(O)OR^5$.

One embodiment provides a compound of Formula (I) or a pharmaceutically acceptable salt thereof, wherein $R^1$ is a heterocyclyl, optionally substituted with one to five substituents independently selected from $C_1$ to $C_6$ alkyl, $C_1$ to $C_4$ haloalkyl, —$OR^4$, and/or halogen. Suitable heterocyclyls include 1- to 2-ring heterocyclyls having 1 to 4 heteroatoms independently selected from O, N, and/or S. Other suitable heterocyclyls include 1-ring heterocyclyls having 1 to 2 heteroatoms independently selected from O, N, and/or S. Examples of suitable heterocyclyl groups include saturated heterocyclyl groups, such as oxetanyl, thiatanyl, azetidinyl, tetrahydrofuran, tetrahydrothiophenyl, pyrrolidinyl, tetrahydropyranyl, teterahydrothiopyranyl, piperidinyl, morpholinyl, piperazinyl. Other examples of suitable heterocyclyl groups include partially unsaturated heterocyclyl groups include 3,4-dihydro-2H-pyrayl, 5,6-dihydro-2H-pyranyl, 2H-pyranyl, 1,2,3,4-tetrahydropyridinyl, and 1,2,5,6-tetrahydropyridinyl. For example, this embodiment provides compounds of Formula (I) wherein n is zero or 1. Preferably, $R^3$ is $C_1$ to $C_6$ alkyl, $C_3$ to $C_8$ cycloalkyl, $C_1$ to $C_6$ haloalkyl, or —$C(O)OR^5$; and more preferably, $R^3$ is $C_1$ to $C_4$ alkyl, $C_1$ to $C_2$ haloalkyl, or —$C(O)OR^5$ wherein $R^5$ is methyl or ethyl.

One embodiment provides a compound of Formula (I) or a pharmaceutically acceptable salt thereof, wherein $R^1$ is a heteroaryl, optionally substituted with one to five substituents independently selected from $C_1$ to $C_6$ alkyl, $C_1$ to $C_4$ haloalkyl, —$OR^4$, and/or halogen. Suitable heteroaryls include 1- to 2-ring heteroaryls having 1 to 4 heteroatoms independently selected from O, N, and/or S. Other suitable heteroaryls include 1-ring heteroaryls having 1 to 4 heteroatoms independently selected from O, N, and/or S. Examples of suitable heteroaryl groups include 1-ring heteroaryl groups such as pyrrolyl, furanyl, thiophenyl, pyrazolyl, imidazolyl, isoxazolyl, oxazolyl, isothiazolyl, thiazolyl, triazolyl, oxadiazolyl, thiadiazolyl, tetrazolyl, pyridinyl, pyridazinyl, pyrimidinyl, and pyrazinyl. Other examples of suitable heteroaryl groups include 2-ring heteroaryl groups such as benzofuranyl, benzothiophenyl, indolyl, benzimidazolyl, indazolyl, benzotriazolyl, pyrrolopyridinyl, imidazopyridinyl, pyrazolopyrdinyl, isoindolyl, indazolyl, purinyl, indolininyl, imidazopyridinyl, pyrazolopyridinyl, and imidazolylpyrimidinyl. For example, this embodiment provides compounds of Formula (I) wherein n is zero or 1. Preferably, $R^3$ is $C_1$ to $C_6$ alkyl, $C_3$ to $C_8$ cycloalkyl, $C_1$ to $C_6$ haloalkyl, or —$C(O)OR^5$; and more preferably, $R^3$ is $C_1$ to $C_4$ alkyl, $C_1$ to $C_2$ haloalkyl, or —$C(O)OR^5$ wherein $R^5$ is methyl or ethyl.

One embodiment provides compounds of Formula (I) or pharmaceutically acceptable salts thereof, wherein $R^3$ is a 1-ring heteroaryl, optionally substituted with one to five substituents independently selected from $C_1$ to $C_6$ alkyl, $C_1$ to $C_4$ haloalkyl, —$OR^4$, and/or halogen. For example, this embodiment provides compounds of Formula (I) wherein $R^3$ is optionally substituted with one to three substituents. This embodiment also provides compounds of Formula (I) wherein $R^3$ is substituted with zero or one substituent.

One embodiment provides compounds of Formula (I) or pharmaceutically acceptable salts thereof, wherein $R^3$ is pyridinyl, optionally substituted with one to five substituents independently selected from $C_1$ to $C_6$ alkyl, $C_1$ to $C_4$ haloalkyl, —$OR^4$, and/or halogen. Compounds of this embodiment include compounds of Formula (Ic):

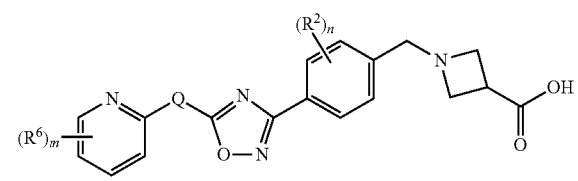

(Ic)

wherein:

Q is

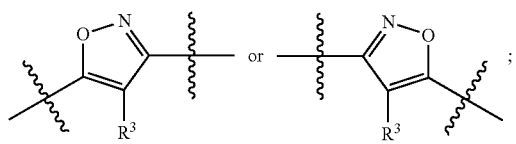

n is zero or an integer selected from 1 through 4;

each $R^2$ is independently selected from hydrogen, $C_1$ to $C_6$ alkyl, $C_1$ to $C_4$ haloalkyl, —$OR^4$, and/or halogen;

$R^3$ is hydrogen, $C_1$ to $C_6$ alkyl, $C_3$ to $C_8$ cycloalkyl, $C_1$ to $C_6$ haloalkyl, or —$C(O)OR^5$;

each $R^4$ is independently selected from $C_1$ to $C_6$ alkyl, $C_1$ to $C_4$ haloalkyl, and/or benzyl;

$R^5$ is $C_1$ to $C_6$ alkyl or benzyl; m is zero or an integer selected from 1 through 4; and each $R^6$ is independently selected from $C_1$ to $C_6$ alkyl, $C_1$ to $C_4$ haloalkyl, halogen, and/or —$OR^4$.

Preferably, $R^3$ is $C_1$ to $C_6$ alkyl, $C_3$ to $C_8$ cycloalkyl, $C_1$ to $C_6$ haloalkyl, or —$C(O)OR^5$. For example, this embodiment provides compounds of Formula (I) wherein n is zero or 1. Preferably, $R^3$ is $C_1$ to $C_6$ alkyl, $C_3$ to $C_8$ cycloalkyl, $C_1$ to $C_6$ haloalkyl, or —$C(O)OR^5$; and more preferably, $R^3$ is $C_1$ to $C_4$ alkyl, $C_1$ to $C_2$ haloalkyl, or —$C(O)OR^5$ wherein $R^5$ is methyl or ethyl.

One embodiment provides compounds of Formula (Ic) or pharmaceutically acceptable salts thereof, wherein n is zero. Compounds of this embodiment include compounds of Formula (Id):

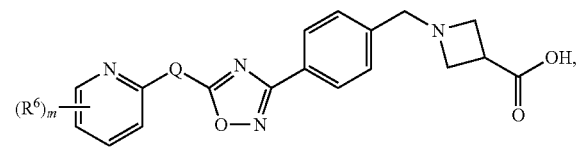

(Id)

wherein:
Q is

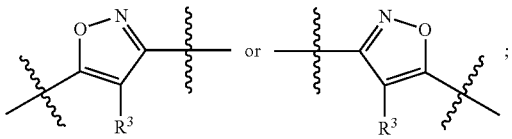

m is zero or an integer selected from 1 through 4;
each $R^6$ is independently selected from $C_1$ to $C_6$ alkyl, $C_1$ to $C_4$ haloalkyl, halogen, and/or —$OR^4$;
each $R^4$ is independently $C_1$ to $C_4$ alkyl; $R^3$ is $C_1$ to $C_6$ alkyl, $C_1$ to $C_4$ haloalkyl, or —$C(O)OR^5$; and
$R^5$ is $C_1$ to $C_4$ alkyl.
In one example of this embodiment, m is 0; and $R^3$ is hydrogen, ethyl, 1-propyl, 2-propyl, —$CF_3$, or —$C(O)OCH_3$.

One embodiment provides a compound of Formula (I) or a pharmaceutically acceptable salt thereof, selected from the group consisting of:
1-(4-(5-(3-(pyridin-2-yl)-4-(trifluoromethyl)isoxazol-5-yl)-1,2,4-oxadiazol-3-yl)benzyl)azetidine-3-carboxylic acid;
1-(4-(5-(5-(pyridin-2-yl)-4-(trifluoromethyl)isoxazol-3-yl)-1,2,4-oxadiazol-3-yl)benzyl)azetidine-3-carboxylic acid;
1-(4-(5-(4-propyl-5-(pyridin-2-yl)isoxazol-3-yl)-1,2,4-oxadiazol-3-yl)benzyl)azetidine-3-carboxylic acid;
1-(4-(5-(4-isopropyl-5-(pyridin-2-yl)isoxazol-3-yl)-1,2,4-oxadiazol-3-yl)benzyl)azetidine-3-carboxylic acid;
1-(4-(5-(4-ethyl-5-(pyridin-2-yl)isoxazol-3-yl)-1,2,4-oxadiazol-3-yl)benzyl)azetidine-3-carboxylic acid;
1-(4-(5-(4-propyl-3-(pyridin-2-yl)isoxazol-5-yl)-1,2,4-oxadiazol-3-yl)benzyl)-azetidine-3-carboxylic acid;
1-(4-(5-(4-(methoxycarbonyl)-3-(pyridin-2-yl)isoxazol-5-yl)-1,2,4-oxadiazol-3-yl)benzyl)azetidine-3-carboxylic acid; and
1-(4-(5-(3-(pyridin-2-yl)isoxazol-5-yl))-1,2,4-oxadiazol-3-yl)benzyl)azetidine-3-carboxylic acid. The compounds of this embodiment may be provided as 2,2,2-trifluoroacetic acid salts.

One embodiment provides a composition comprising a compound according to Formula (I) or a pharmaceutically acceptable salt thereof; and a pharmaceutically acceptable carrier.

One embodiment provides a method of treating a disease or disorder associated with the activity of G protein-coupled receptor $S1P_1$, the method comprising administering to a mammalian patient of a compound of Formula (I) or a pharmaceutically acceptable salt thereof, wherein:
Q is

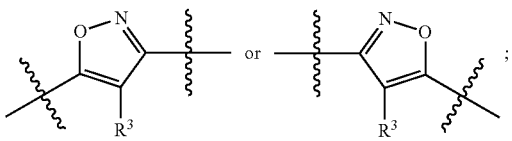

n is zero or an integer selected from 1 through 4;
$R^1$ is cycloalkyl, heteroaryl, or heterocyclyl, each optionally substituted with one to five substituents independently selected from $C_1$ to $C_6$ alkyl, $C_1$ to $C_4$ haloalkyl, —$OR^4$, and/or halogen;
each $R^2$ is independently selected from hydrogen, $C_1$ to $C_6$ alkyl, $C_1$ to $C_4$ haloalkyl, —$OR^4$, and/or halogen;
$R^3$ is hydrogen, alkyl, cycloalkyl, haloalkyl, or —$C(O)OR^5$;
each $R^4$ is independently selected from $C_1$ to $C_6$ alkyl, $C_1$ to $C_4$ haloalkyl, and/or benzyl; and
$R^5$ is alkyl or benzyl.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, or I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_1$-$C_6$ alkyl" denotes straight and branched chain alkyl groups with one to six carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$), and 2,2,2-trifluoroethyl (—$CH_2CF_3$). When numbers appear in a subscript after the symbol "C", the subscript defines with more specificity the number of carbon atoms that a particular haloalkyl group may contain. For example, "$C_1$-$C_4$ haloalkyl" denotes straight and branched chain haloalkyl groups with one to four carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$).

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "heteroatom" as used herein refers to oxygen, sulfur, and nitrogen.

The term "heterocyclyl" as used herein refers to non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" as used herein refers to aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

Exemplary tricyclic heteroaryl groups include carbazolyl, benzidolyl, phenanthrollinyl, acridinyl, phenanthridinyl, and xanthenyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) Wermuth, C. G. et al., *The Practice of Medicinal Chemistry*, Chapter 31, Academic Press (1996);
b) *Design of Prodrugs*, Bundgaard, H. ed., Elsevier (1985);
c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and
d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent vascular disease or autoimmune diseases.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant and vehicle. Alternate compositions of this invention comprise a compound of the Formula (I) described herein, or a pharmaceutically acceptable salt thereof, and a pharmaceutically acceptable carrier, adjuvant or vehicle.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

UTILITY

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds which act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology*, 28:102 (2007)).

By virtue of their $S1P_1$ activity as agonists, the compounds of the present invention are immuno-regulatory agents useful for treating or preventing autoimmune or chronic inflammatory diseases. The compounds of the present invention are useful to suppress the immune system in instances where immuno-suppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also embodied within the present invention is a method of preventing or treating resistance to transplantation or transplantation rejection of organs or tissues in a mammalian patient in need thereof, which comprises administering a compound of Formula (I) or a pharmaceutically acceptable salt thereof. A therapeutically effective amount for preventing or treating resistance to transplantation or transplantation rejection may be administered.

A method of suppressing the immune system in a mammalian patient in need thereof, which comprises administering to the patient a compound of Formula (I) or a pharmaceutically acceptable salt thereof, is yet another embodiment. A therapeutically effective amount for suppressing the immune system may be administered.

Most particularly, the method described herein encompasses a method of treating or preventing bone marrow or organ transplant rejection which is comprised of administering to a mammalian patient in need of such treatment or prevention a compound of Formula (I) or a pharmaceutically acceptable salt thereof. A therapeutically effective amount for treating or preventing bone marrow or organ transplant rejection may be administered.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis, and ischemia reperfusion injury.

The methods of treating $S1P_1$-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the $S1P_1$ receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo[1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), or their ligands including CD154 (GP39, or CD40L); antibodies to, fusion proteins, or soluble receptors of human cytokines or growth factors, for example, TNF such as, infliximab (REMICADE®), etanercept (ENBREL®), adalimumab (HUMIRA®), LT, Il-1 such as anakinra (KINERET®) (an IL-1 receptor antagonist), IL-2, IL-4, IL-5, Il-6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as compounds of Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, the oxadiazole compounds of the present invention (1.4) may be prepared through the reaction of carboxylic acids (1.1) with N'-hydroxybenzimidamides (1.2) with a variety of coupling reagents (e.g., EDC, HOBt, BOP, BOP—Cl). Alternatively, the N'-hydroxybenzimidamides may be reacted with acid fluoride (1.5) or acid chloride compounds (1.6). In each case, the initially formed N'-acyloxybenzimidamides (1.3) may spontaneously convert to the oxadiazoles under the reaction conditions. In cases where the N'-acyloxybenzimidamide (1.3) does not cyclize spontaneously, it may be isolated and subjected to reaction conditions to effect the cyclodehydration to 1.4. Such conditions may include heating (either conventional or microwave), or treatment with fluoride source (such as tetrabutyl ammonium fluoride).

Scheme 1

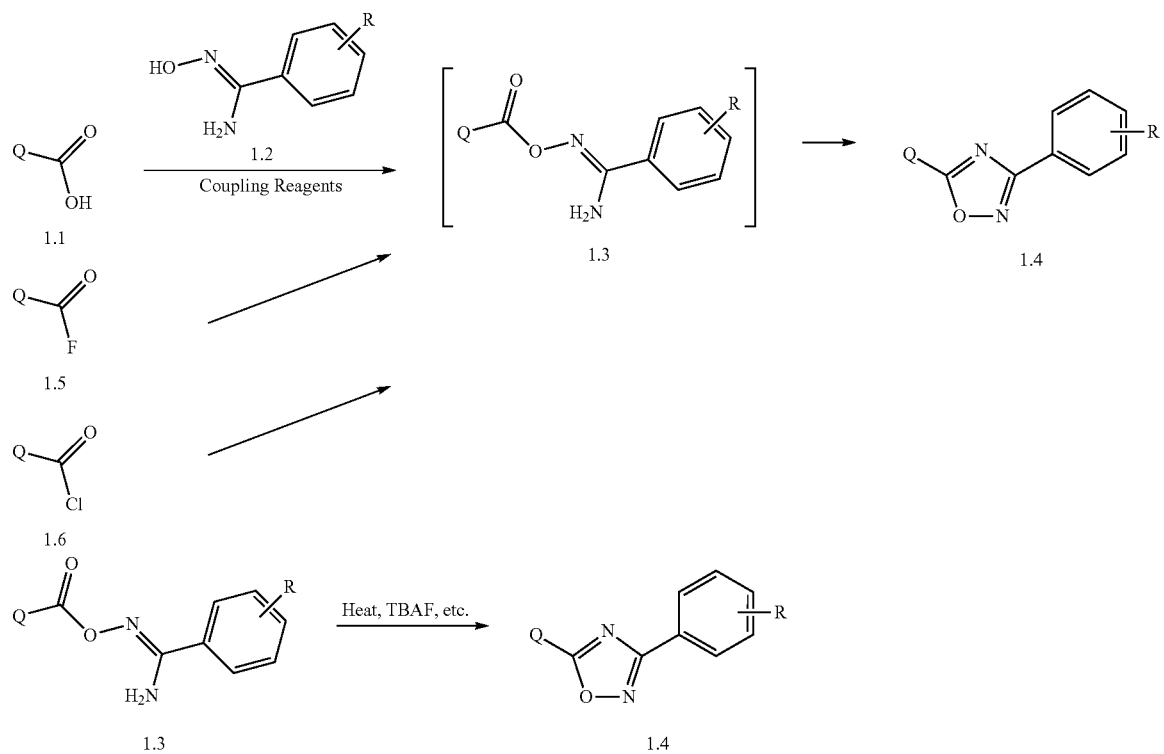

Compounds of formula (I) may be prepared through the reaction of acids (1.1) acid fluorides (1.5) or acid chlorides (1.6) with (Z)-tert-butyl 1-(4-(N'-hydroxycarbamimidoyl)benzyl)azetidine-3-carboxylate (2.1) via means described above to produce compounds of structure 2.2. Deprotection of tert-butyl ester derivatives (2.2) by treatment with an acid (for example trifluoroacetic acid) provides compounds of formula (I).

Scheme 2

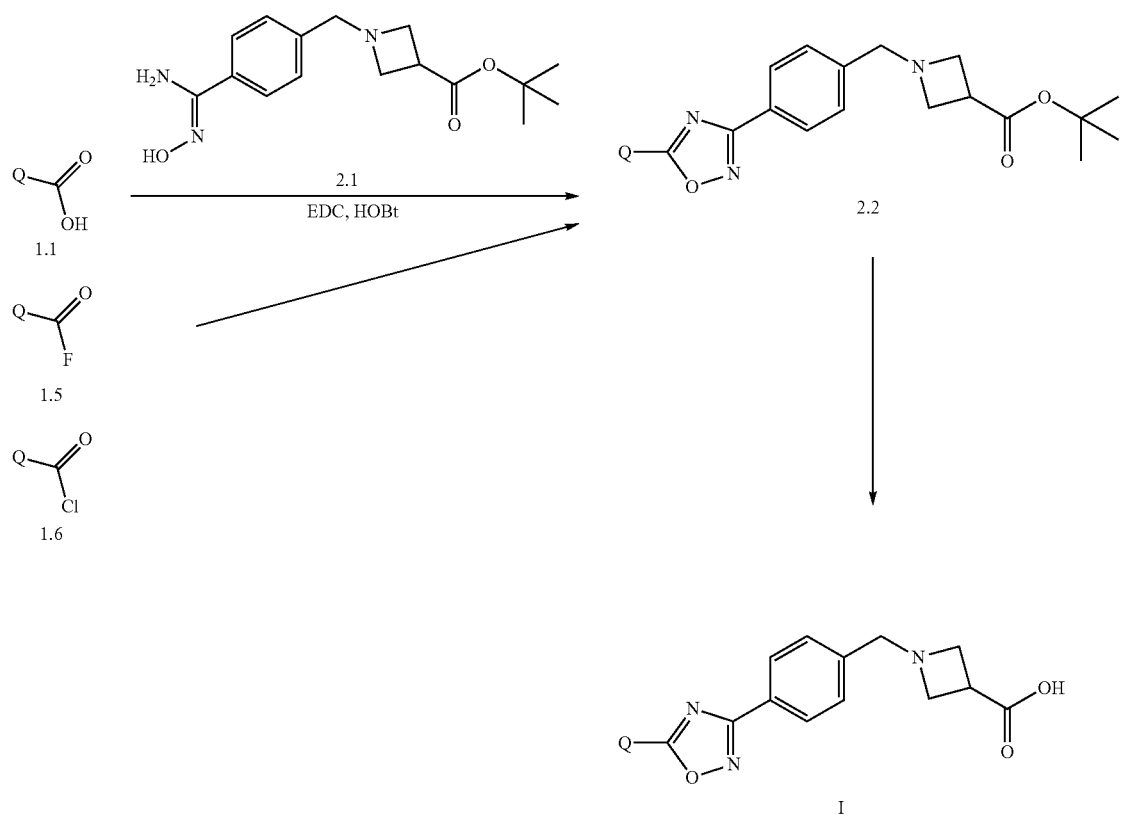

Alternatively, compounds of formula (I) may also be produced as described in Scheme 3. The reaction of acids (1.1) acid fluorides (1.5) or acid chlorides (1.6) with (Z)—N'-hydroxy-4-(hydroxymethyl)benzimidamide (3.2) via means described above can produce compounds of structure 3.3 which, after oxidation to the corresponding aldehyde (3.4), can undergo reductive amination with azetidine-3-carboxylic acid (3.5) or tert-butyl azetidine-3-carboxylate (3.6) to provide a compound of formula (I) or 2.2 respectively. Compound 2.2 may be converted to a compound of formula (I) as described above. The reaction of acids (1.1) acid fluorides (1.5) or acid chlorides (1.6) with (Z)—N'-hydroxy-4-(methyl)benzimidamide (3.7) via means described above can produce compounds of structure 3.8 which can be halogenated on the benzyllic position (for example with N-bromosuccinimide) to provide 3.9. Reaction of 3.9 with azetidine-3-carboxylic acid (3.5) or tert-butyl azetidine-3-carboxylate (3.6) provides a compound of formula (I) or 2.2 respectively.

Scheme 3

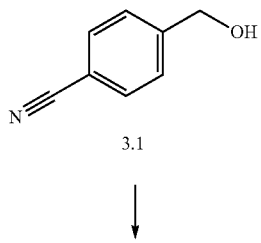

-continued

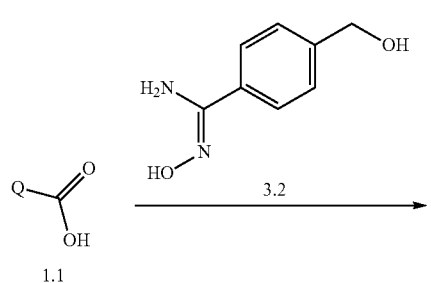
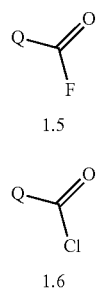
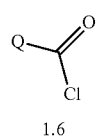
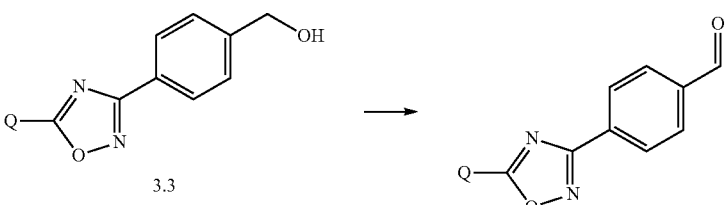
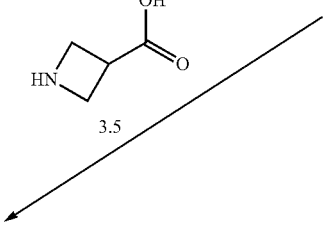
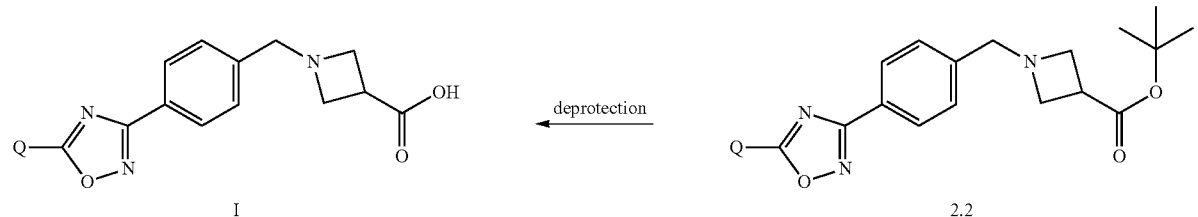
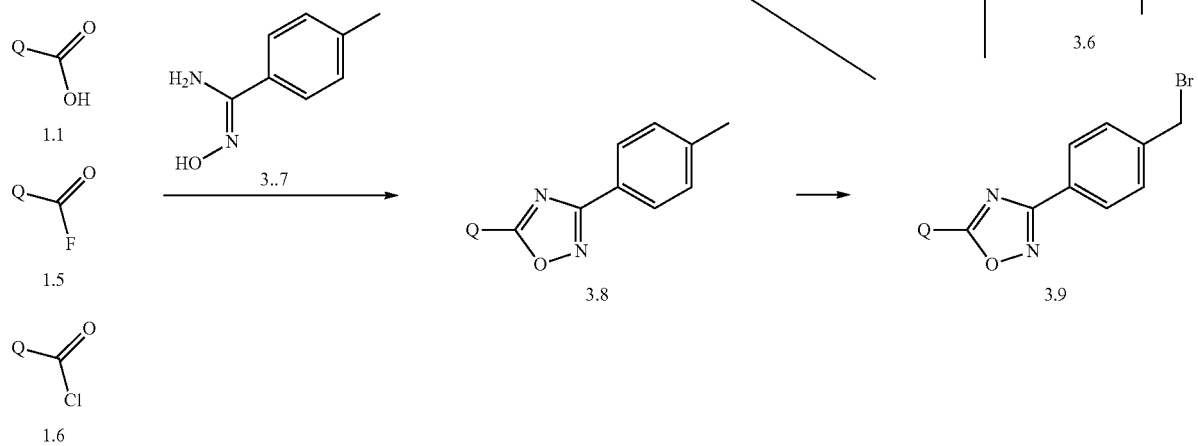

tert-Butyl azetidine-3-carboxylate (3.6) may be prepared from azetidine-3-carboxylic acid (3.5) via protection of the amine (for example with the CBZ group) followed by esterification of the acid with tert-butyl alcohol in the presence of a coupling reagent (for example CDI) and then removal of the amine protecting group. (Z)-tert-Butyl 1-(4-(N'-hydroxycarbamimidoyl)benzyl)azetidine-3-carboxylate (2.1) is available from the reaction of tert-butyl azetidine-3-carboxylate (3.6) with 4-formylbenzonitrile (4.2) under reducing conditions to give 4.3, which is then reacted with hydroxylamine. Alternatively, compound 4.3 may be prepared by esterification of 4.5, which is obtained from the reaction of azetidine-3-carboxylic acid (3.5) with 4-formylbenzonitrile (4.2) under reducing conditions.

Scheme 4

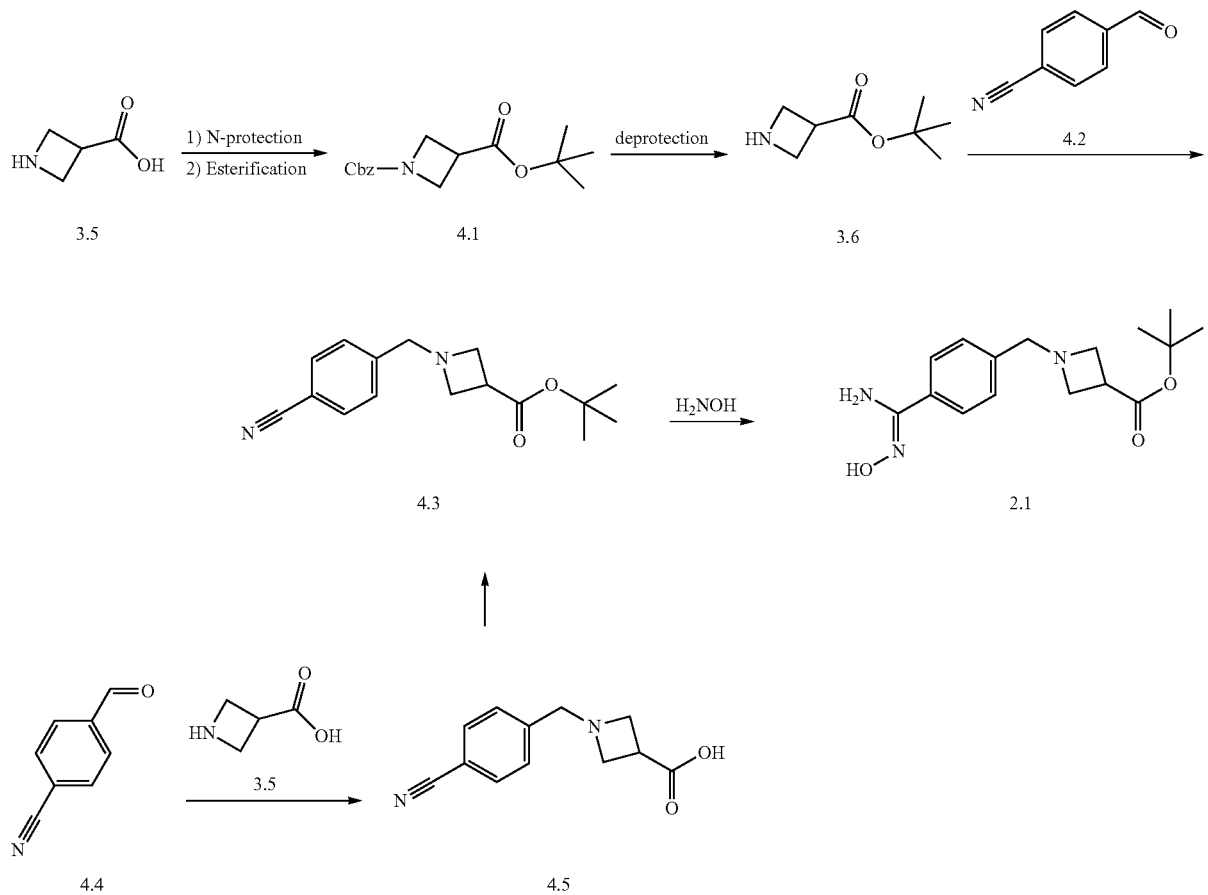

The carboxylic acid fragments (1.1) of the present invention may be prepared by a variety of methods, including those illustrated in Scheme 5 for the isoxazoles bearing the carboxylic acid group at the 5-position. Reaction of chloro-oxime 5.1 with substituted propiolates (5.2) under basic conditions provides a mixture of isoxazole carboxylates (5.3/5.4) generally in favor of isomer 5.3. After separation of the isomers (such as by silica gel chromatography or reverse phase preparative HPLC), 5.4 may be hydrolyzed to give the required isoxazole carboxylic acid (5.5). Reaction of chloro-oxime 5.1 with substituted propargylic alcohols (5.6) under basic conditions provides a mixture of isoxazole carboxylates (5.7/5.8) generally in favor of isomer 5.8. After separation of the isomers (such as by silica gel chromatography or reverse phase preparative HPLC), 5.8 may be oxidized to give acid 5.5. Esters 5.4 may also be obtained regioselectively through the reaction of 5.1 with substituted 2-bromo-acrylates (5.9). When chloro-oximes 5.1 are reacted with unsubstituted propiolates (5.10), isoxazoles 5.12 are produced regioselectively. The unsubstituted isoxazole position may then be converted to a halogenated derivative (5.13) which may then be used for further transformations including but not limited to transition metal cross coupling reactions or insertion reaction. In this fashion, 4-trifluoromethyl isoxazoles (5.14) may be obtained through the reaction of 4-bromoisoxazoles 5.13 with a various trifluoromethylating reagents (for example methyl 2,2-difluoro-2-(fluorosulfonyl)acetate/copper (I) iodide, or methyl 2-chloro-2,2-difluoroacetate/potassium fluoride/copper (I) iodide, or trimethyl(trifluoromethyl)silane/potassium fluoride/copper (I) iodide).

Scheme 5

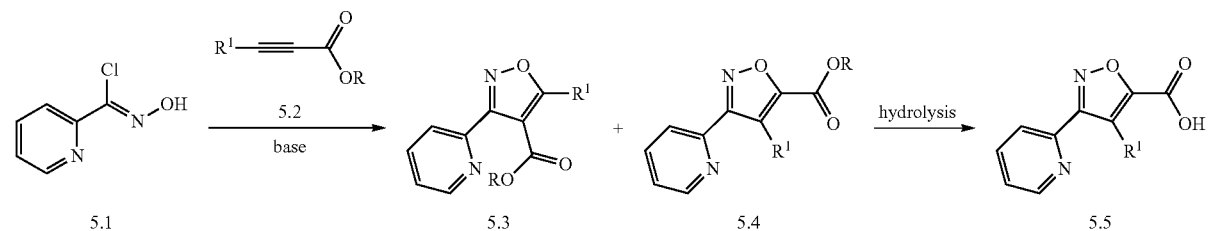

-continued

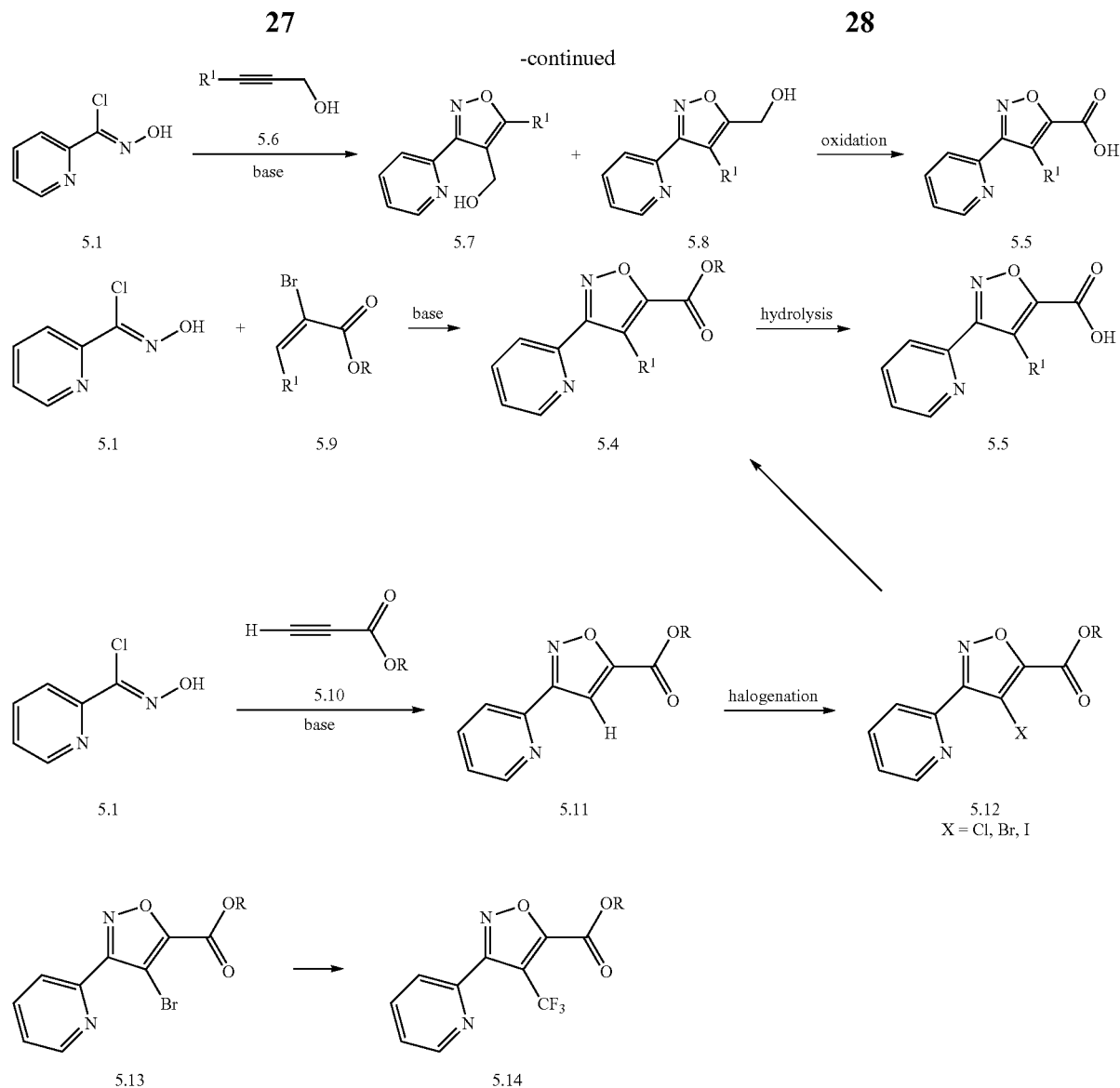

Illustrated in Scheme 6 are approaches for the isoxazoles bearing the carboxylic acid group at the 3-position. Isoxazole-3-carboxylic esters (6.3) may be prepared from the reaction of internal alkynes (6.1) with dimethyl 2-nitromalonate (6.2) under thermal decomposition conditions (heating in an inert solvent) or reaction with chloro-oximes 6.5 under basic conditions. Hydrolysis of the esters (6.3) then provides the acids (6.4). The reaction of terminal alkynes (6.8) with chloro-oximes 6.5 leads to isoxazole esters lacking substitution at the 4-position. The unsubstituted isoxazole position may then be converted to a halogenated derivative (6.7) which may then be used for further transformations including but not limited to transition metal cross coupling reactions or insertion reaction to provide access to compounds 6.3.

Scheme 6

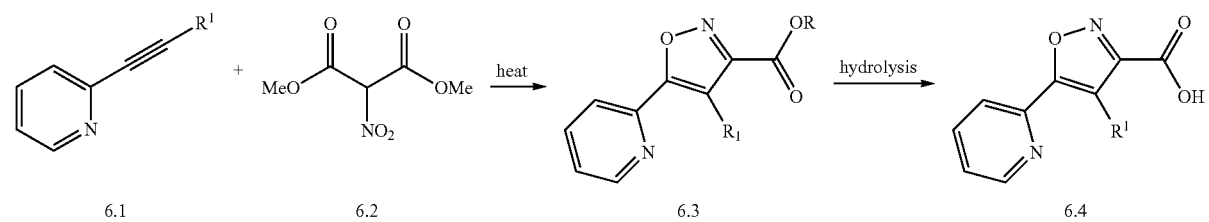

-continued

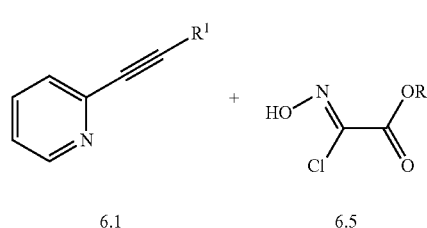
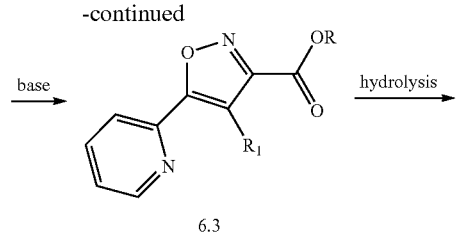

6.1   6.5   6.3   6.4

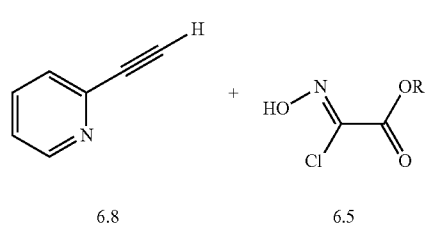
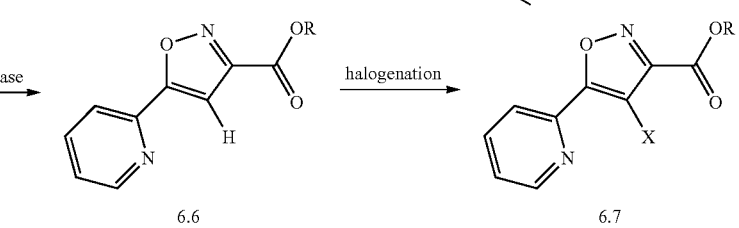

6.8   6.5   6.6   6.7
X = Cl, Br, I

| ABBREVIATIONS | |
|---|---|
| Ac | acetyl |
| AcOH | acetic acid |
| aq. | aqueous |
| CDI | carbonyldiimidazole |
| Bn | benzyl |
| Bu | butyl |
| Boc | tert-butoxycarbonyl |
| DMAP | dimethylaminopyridine |
| DMA | N,N-dimethylacetamide |
| DMF | dimethylformamide |
| DMSO | dimethylsulfoxide |
| EDC | 1-(3-Dimethylaminopropyl)-3-ethylcarbodiimide hydrochloride |
| EtOAc | ethyl acetate |
| Et | ethyl |
| EtOH | ethanol |
| H | hydrogen |
| h | hour(s) |
| i | iso |
| HPLC | high pressure liquid chromatography |
| HOAc | acetic acid |
| LC | liquid chromatography |
| Me | methyl |
| MeOH | methanol |
| min. | minute(s) |
| $M^{+1}$ | $(M + H)^+$ |
| MS | mass spectrometry |
| n | normal |
| PhCONCS | benzyolyisothiocyanate |
| Pd/C | palladium on carbon |
| Ph | phenyl |
| Pr | propyl |
| PSI | pounds per square inch |
| Ret Time | retention time |
| rt or RT | room temperature |
| sat. | saturated |
| t | tertiary |
| TFA | trifluoroacetic acid |
| THF | tetrahydrofuran |
| Phenomenex | Phenomenex, Macclesfield, Cheshire, UK |
| YMC | YMC, Inc, Wilmington, NC 20403 |

EXAMPLES

The following Examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc. and are abbreviated as Int. 1, Int. 2, etc. In some instances the preparation of common intermediates may require multiple steps to be prepared. Each step is identified by the common intermediate and the step (e.g., Int. 1-A, Int. 1-B, and so forth. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or Examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the Examples of this invention.

Those experiments specifying that they were performed in a microwave oven were conducted in a SmithSynthesizer oven manufactured by Personal Chemistry or a Discover microwave oven manufactured by CEM corporation. The microwave ovens generate a temperature which can be selected to be between 60-250° C. The microwave ovens automatically monitor the pressure which is between 0-300 PSI. Reaction hold times and temperature set points are reported.

Preparation of Intermediate 1 (Int. 1)

tert-Butyl 1-(4-(N'-hydroxycarbamimidoyl)-benzyl)azetidine-3-carboxylate

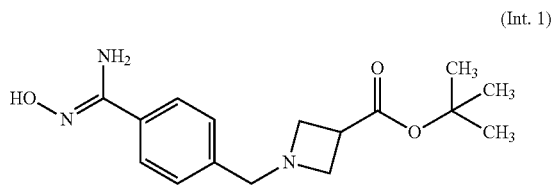 [SMILES: CC(C)(C)OC(=O)C1CN(Cc2ccc(/C(N)=N/O)cc2)C1]

(Int. 1)

Int. 1-A.
1-(Benzyloxycarbonyl)azetidine-3-carboxylic acid

(Int. 1-A)

To a solution of azetidine-3-carboxylic acid (88 g, 0.871 mol) and sodium bicarbonate (161 g, 1.92 mol) in water (1.75 L) at room temperature was added a solution of benzyl 2,5-dioxopyrrolidin-1-ylcarbonate (239 g, 0.959 mol) in tetrahydrofuran (3.5 L). The reaction mixture was stirred at room temperature overnight. The solvent was removed under reduced pressure, and the aqueous layer was washed with ethyl acetate (2×500 mL). The aqueous layer was acidified with a 1.0 N aqueous solution of hydrochloric acid and extracted with ethyl acetate (3×750 mL). The organic layer was washed with water, washed with brine, and dried over anhydrous sodium sulfate. Concentration under reduced pressure afforded 1-(benzyloxycarbonyl)azetidine-3-carboxylic acid as colorless oil (202 g, 99% yield). The compound had an HPLC retention time=2.27 min.—Column: YMC COMBISCREEN® ODS-A 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=236.15. $^1$H NMR (400 MHz, $CDCl_3$) δ ppm 3.39-3.49 (m, 1H), 4.22 (d, J=7.28 Hz, 4H), 5.11 (s, 2H), and 7.29-7.39 (m, 5H).

Int. 1-B. 1-Benzyl 3-tert-butyl azetidine-1,3-dicarboxylate

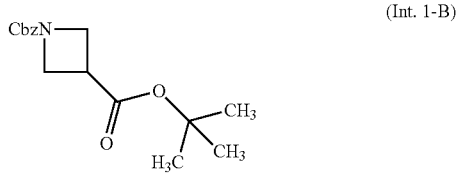 [SMILES: CC(C)(C)OC(=O)C1CN(C(=O)OCc2ccccc2)C1]

(Int. 1-B)

To a solution of 1-(benzyloxycarbonyl)azetidine-3-carboxylic acid (200 g, 0.851 mol) in dichloromethane (6.0 L) at 0° C. was added t-butanol (158 g, 2.13 mol), DMAP (52.0 g, 0.425 mol), and EDCI (163 g, 0.853 mol). The reaction was stirred at room temperature overnight. The reaction mixture was concentrated, and the residue was dissolved in ethyl acetate, washed with a 10% aqueous solution of citric acid, washed with a 10% aqueous solution of sodium bicarbonate, washed with brine, and dried over anhydrous sodium bicarbonate. Concentration under reduced pressure afforded 1-benzyl-3-tert butyl-azetidine-1,3-dicarboxylate (200 g, 81% yield) as a colorless oil. The compound had an HPLC retention time=3.27 min.—Column: YMC COMBISCREEN® ODS-A 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=292.15. $^1$H NMR (400 MHz, $CDCl_3$) δ ppm 1.46 (s, 9H), 3.24-3.33 (m, 1H), 4.14 (d, J=7.53 Hz, 4H), 5.10 (s, 2H), and 7.30-7.39 (m, 5H).

Int. 1-C. tert-Butyl azetidine-3-carboxylate

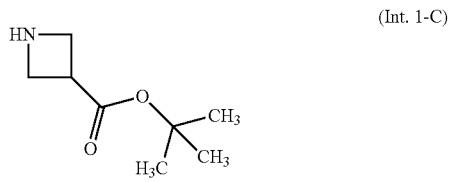

(Int. 1-C)

A mixture of 1-benzyl-3-tert-butyl-azetidine-1,3-dicarboxylate (140 g, 0.480 mol) and 10% palladium on carbon (28.0 g) in ethyl acetate (1.40 L) was placed in an autoclave under 3.0 kg/cm² of hydrogen pressure overnight. The reaction mixture was filtered through CELITE®, and the CELITE® bed was washed with ethyl acetate. Acetic acid (28.9 g, 0.480 mol) was added to the filtrate, and it was concentrated under reduced pressure maintaining the temperature below 50° C. to give tert-butyl azetidine-3-carboxylate acetic acid salt (96 g, 92% yield) as a colorless oil. $^1$H NMR (400 MHz, $CDCl_3$) δ ppm 1.47 (s, 9H), 2.02 (s, 3H), 3.52-3.63 (m, 1H), and 4.00-4.10 (m, 4H).

Int. 1-D. tert-Butyl 1-(4-cyanobenzyl)azetidine-3-carboxylate

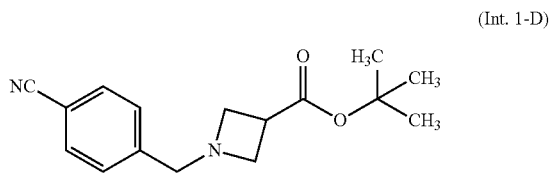 [SMILES: CC(C)(C)OC(=O)C1CN(Cc2ccc(C#N)cc2)C1]

(Int. 1-D)

To a solution of tert-butyl azetidine-3-carboxylate acetic acid salt (92.0 g, 0.423 mol) in methanol (1.0 L) at room temperature was added 4-formylbenzonitrile (50.8 g, 0.381 mol). The reaction mixture was cooled to 0° C., and sodium cyanoborohydride (28.8 g, 0.458 mol) was added portionwise (caution: potential cyanide generation). The reaction mixture was allowed to warm to room temperature and was stirred overnight. The reaction mixture was concentrated under reduced pressure, and the residue was diluted with a 10% aqueous solution of sodium bicarbonate and extracted with ethyl acetate. The organic layer was collected, washed with brine, and dried over anhydrous sodium sulfate. Concentration under reduced pressure followed by purification by silica gel chromatography using a 20% mixture of ethyl acetate in petroleum ether afforded tert-butyl 1-(4-cyanobenzyl)azetidine-3-carboxylate (89%) (After chromatography, Int. 1-D contained a small amount of 4-hydroxymethylbenzonitrile but was taken forward to the next step without further purification). LC/MS $M^{+1}$=273.18. $^1$H NMR (400 MHz, CDCl₃) δ ppm 1.46 (s, 9H), 3.22-3.31 (m, 3H), 3.48-3.56 (m, 2H), 3.66 (s, 2H), 7.39 (d, J=8.28 Hz, 2H), and 7.60 (d, J=8.28 Hz, 2H).

Int. 1. Preparation of tert-butyl 1-(4-(N'-hydroxycarbamimidoyl)benzyl)azetidine-3-carboxylate

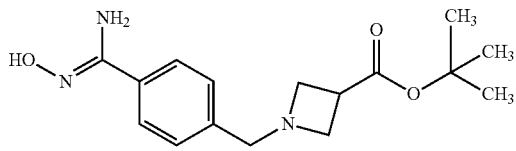

(Int. 1)

To tert-butyl-1-(4-cynaobenzyl)azetidine-3-carboxylate (89.0 g, 0.326 mol) in tert-butanol (1.30 L), was added sodium bicarbonate (109.8 g, 1.31 mol) and hydroxylamine hydrochloride (45.5 g, 0.654 mol). The reaction was heated at reflux for 7 h and then cooled to room temperature and stirred overnight. The reaction mixture was diluted with water and extracted with ethyl acetate. The organic layer was collected, washed with water, washed with brine, and dried over anhydrous sodium sulfate. Concentration followed by purification by silica gel chromatography using 2.5% methanol in chloroform containing 0.2% triethylamine as eluent afforded tert-butyl 1-(4-(N'-hydroxycarbamimidoyl)benzyl)azetidine-3-carboxylate (64 g, 0.210 mol, 55% yield over 2 steps). The compound had an HPLC retention time=7.03 min.—Column: XBridge Phenyl 150×4.6 mm 3.5 u, SC/749. 1 mL/min. Solvent A=5% MeCN, 95% H₂O, 0.05% TFA; Solvent B=95% MeCN, 5% H₂O, 0.05% TFA. Time/% B: 0 min/0%, 15 min/50%, 18 min/100%, 20 min/100%. LC/MS M⁺¹=306.2. ¹H NMR (400 MHz, CDCl₃) δ ppm 1.45 (s, 9H), 3.23-3.30 (m, 3H), 3.49-3.57 (m, 2H), 3.63 (s, 2H), 4.85 (s, 2H), 7.31 (d, J=8.28 Hz, 2H), and 7.57 (d, J=8.28 Hz, 2H).

Alternative Preparation of Int. 1-D. tert-Butyl 1-(4-cyanobenzyl)azetidine-3-carboxylate

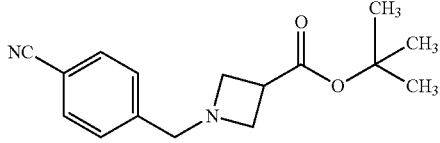

(Int. 1-D)

Int. 1-E. 1-(4-Cyanobenzyl)azetidine-3-carboxylic acid

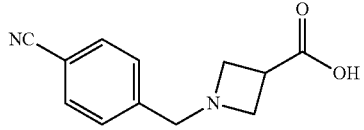

(Int. 1-E)

A mixture of 4-formylbenzonitrile (2.88 g, 22.0 mmol), azetidine-3-carboxylic acid (2.02 g, 20 mmol), and acetic acid (1.15 mL, 20.0 mmol) in dichloromethane (20 mL) and methanol (80 mL) was stirred at room temperature for 1 h. Sodium triacetoxyborohydride (6.78 g, 32.0 mmol) was added and stirring was continued at room temperature for 18 hr. The volatiles were removed under reduced pressure, and the residue was partitioned between water (50 mL) and diethyl ether (50 mL). The aqueous layer was collected, washed with diethyl ether (50 mL), and concentrated. The residue was dissolved in water (20 mL) and loaded onto a 2.5×20 cm HP-20 column [Preparation of HP-20 Gel: ~400 ml of dry, unused MCI CHP-20 Gel (75-150 micron) was swelled in methanol for 24 hrs. The gel was filtered and rinsed with 1 liter of methanol. It was then transferred to a bottle for storage under methanol. Immediately before use, the desired amount of gel was rinsed thoroughly with 20 volumes of water]. The column was eluted with 240 mL of water and 400 mL of methanol. The product containing fractions were concentrated and co-evaporated from ethanol and ethyl acetate/heptane to afford 1-(4-cyanobenzyl)azetidine-3-carboxylic acid (3.25 g, 15.0 mmol, 75% yield) as a white solid. MS: (M+H)=217.18. ¹H NMR (400 MHz, MeOD) δ ppm 3.39 (m, 1H), 4.08 (m, 4H), 4.32 (s, 2H), 7.63 (d, J=8.3 Hz, 2H), and 7.82 (d, J=8.3 Hz, 2H).

Int. 1-Alt.D2. tert-Butyl 1-(4-cyanobenzyl)azetidine-3-carboxylate

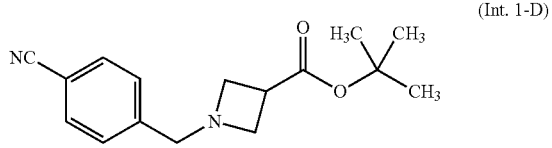 [SMILES: CC(C)(C)OC(=O)C1CN(Cc2ccc(C#N)cc2)C1]

(Int. 1-D)

To a mixture of 1-(4-cyanobenzyl)azetidine-3-carboxylic acid (3.25 g, 15.0 mmol), DMAP (1.84 g, 15.0 mmol), and tert-butanol (14.1 mL, 150 mmol) in dichloroethane (150 mL) was added EDC (4.32 g, 22.5 mmol), and the reaction mixture was allowed to stir over the weekend. The volatiles were removed under reduced pressure, and the residue was partitioned between ethyl acetate (250 mL) and a saturated aqueous solution of sodium bicarbonate (250 mL). The organic layer was washed with water (250 mL), washed with brine (100 mL), and dried over anhydrous magnesium sulfate. Concentration under reduced pressure afforded a light yellow oil which was chromatographed on a 5×15 cm silica gel column, eluting with a 0-40% ethyl acetate/hexane gradient to give tert-butyl 1-(4-cyanobenzyl)azetidine-3-carboxylate (3.5 g, 12.9 mmol, 86% yield) as a colorless liquid. HPLC retention time=1.38 minutes—Column: YMC-Combi 4.6×50 mm S-5 ODS column) eluting with 10-90% aqueous methanol+0.2% phosphoric acid over a 4 minute gradient. MS: (M+H)=273.18. ¹H NMR (400 MHz, CDCl₃) δ ppm 1.46 (s, 9H), 3.26 (m, 3H), 3.52 (m, 2H), 3.66 (s, 2H), 7.39 (d, J=8.3 Hz, 2H), and 7.60 (d, J=8.3 Hz, 2H).

Example 1

1-(4-(5-(3-(Pyridin-2-yl)-4-(trifluoromethyl)isoxazol-5-yl)-1,2,4-oxadiazol-3-yl)benzyl)azetidine-3-carboxylic acid

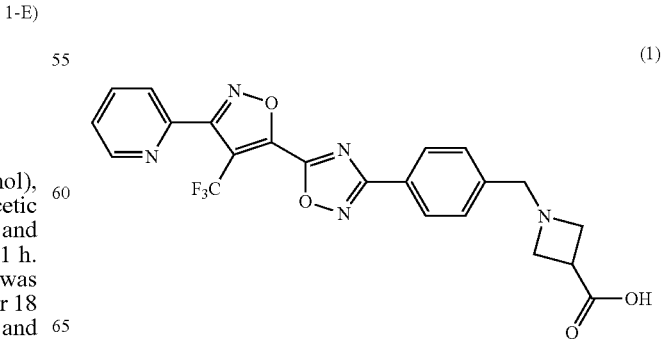

(1)

1-A. N-Hydroxypicolinimidoyl chloride

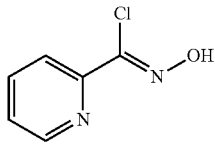
(1-A)

To a colorless, homogeneous solution of (E)-picolinaldehyde oxime (6.75 g, 55.3 mmol) in N,N-dimethylformamide (55 mL) at room temperature was added N-chlorosuccinimide (7.38 g, 55.3 mmol) portion-wise. After the addition of ~⅕ of the NCS, the reaction mixture was immersed in an oil bath at 60° C., and the remaining NCS was added portion-wise over 1.5 h. After the addition was complete, the homogeneous reaction mixture was stirred for 60 min. at 60° C. and was then cooled to room temperature. Water (400 mL) was added, and the aqueous mixture was extracted with ether (3×200 mL). The organic layer was collected, washed with water (2×200 mL), washed with a saturated aqueous solution of brine (100 mL), and dried over anhydrous magnesium sulfate. Concentration under reduced pressure afforded N-hydroxypicolinimidoyl chloride (6.45 g, 41.2 mmol, 75% yield) as a tan solid. The compound had an HPLC retention time=0.515 min.—Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=156.8. $^1$H NMR (400 MHz, $CDCl_3$) δ ppm 7.37-7.43 (m, 1H), 7.80 (td, J=7.78, 1.76 Hz, 1H), 7.91-7.97 (m, 1H), 8.72 (d, J=4.02 Hz, 1H), and 9.85 (br. s., 1H).

1-B. Ethyl 3-(pyridin-2-yl)-4-(trifluoromethyl)isoxazole-5-carboxylate

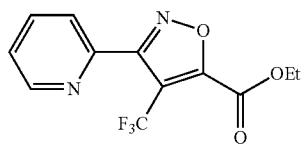
(1-B)

To a yellow, homogeneous mixture of N-hydroxypicolinimidoyl chloride (4.67 g, 29.8 mmol) and ethyl 4,4,4-trifluorobut-2-ynoate (4.50 g, 27.1 mmol) in dichloromethane (90 mL) at room temperature was added triethylamine (7.93 mL, 56.9 mmol) slowly over 30 min. During the addition, the reaction mixture slowly became dark in color. The reaction was stirred overnight at room temperature. The solvent was removed under reduced pressure, and the residue was diluted with ether (100 mL) and washed with water (100 mL). The organic layer was collected, and the aqueous layer was extracted with ether (2×100 mL). The combined organic layers were dried over anhydrous magnesium sulfate and concentrated under reduced pressure. By HPLC, the product mixture contained a ~15:85 mixture of the desired isomer and its regioisomer. The mixture was purified by preparative HPLC, and the desired fractions were concentrated under reduced pressure. The residue was diluted with ethyl acetate (100 mL), washed with a saturated aqueous solution of sodium bicarbonate (100 mL), washed with brine (50 mL), and dried over anhydrous magnesium sulfate. Concentration under reduced pressure afforded ethyl 3-(pyridin-2-yl)-4-(trifluoromethyl)isoxazole-5-carboxylate (0.518 g, 1.81 mmol, 6.7% yield) as a pale yellow, viscous oil. The compound had an HPLC ret. time=2.18 min.—Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=286.9. $^1$H NMR (400 MHz, $CDCl_3$) δ ppm 1.46 (t, J=7.15 Hz, 3H), 4.54 (q, J=7.03 Hz, 2H), 7.46 (ddd, J=7.53, 4.77, 1.25 Hz, 1H), 7.76-7.81 (m, 1H), 7.83-7.89 (m, 1H), and 8.78 (d, J=4.77 Hz, 1H).

An Alternative Preparation of ethyl 3-(pyridin-2-yl)-4-(trifluoromethyl)isoxazole-5-carboxylate (1B)

1-B-1. Ethyl 2,3-dibromo-4,4,4-trifluorobutanoate

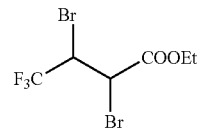
(1-B-1)

Bromine (18.4 mL, 357 mmol) was added dropwise over 30 minutes to a solution of (E)-ethyl 4,4,4-trifluorobut-2-enoate (50 g, 297 mmol) in carbon tetrachloride (50 mL) at room temperature under nitrogen. The resulting dark red solution was refluxed for 4 hours. Additional bromine (2 ml) was added and heating was continued until the HPLC analysis showed that the starting material had been consumed. The reaction mixture was concentrated under reduced pressure to give light brown oil which used in the next step without purification. HPLC (XBridge 5µ C18 4.6×50 mm, 4 mL/min, Solvent A: 10% MeOH/water with 0.2% $H_3PO_4$, Solvent B: 90% MeOH/water with 0.2% $H_3PO_4$, gradient with 0-100% B over 4 minutes): 2.96 and 3.19 minutes.

1-B-2. (Z/E)-Ethyl 2-bromo-4,4,4-trifluorobut-2-enoate

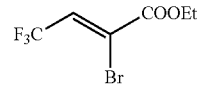
(1-B-2)

To a solution of ethyl 2,3-dibromo-4,4,4-trifluorobutanoate (1-B-1) in hexane (200 mL) cooled to 0° C. was added triethylamine (49.7 ml, 357 mmol) drop-wise over 35 minutes, during which time a white precipitate formed. The reaction mixture was stirred for an additional 2 hours until LC indicated complete conversion. The solid was filtered and rinsed with hexane (3×50 mL), and the filtrate was concentrated and passed through a short silica gel pad eluting with 10% ethyl acetate/hexane to give (Z/E)-ethyl 2-bromo-4,4,4-trifluorobut-2-enoate (65.5 g, 265 mmol, 89% yield for two steps) as a colorless oil. Alternatively, the crude product can be purified by distillation (85° C./~60 mmHg). $^1$H NMR ($CDCl_3$, 400 MHz) δ 7.41 (q, 1H, J=7.28 Hz), 4.35 (q, 2H, J=7.11 Hz), 1.38 (t, 3H, J=7.15 Hz); HPLC (XBridge 5µ C18 4.6×50 mm, 4 mL/min, Solvent A: 10% MeOH/water with 0.2% H₃PO₄, Solvent B: 90% MeOH/water with 0.2% H₃PO₄, gradient with 0-100% B over 4 minutes): 3.09 minutes.

1-B. Alternative Preparation of ethyl 3-(pyridin-2-yl)-4-(trifluoromethyl)isoxazole-5-carboxylate

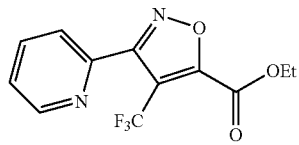

(1-B)

To a solution of (Z)-ethyl 2-bromo-4,4,4-trifluorobut-2-enoate (1.58 g, 6.39 mmol) and (E,Z)—N-hydroxypicolinimidoyl chloride (2.0 g, 12.8 mmol) in ethyl acetate (10 mL) was added indium (III) chloride (0.283 g, 1.28 mmol). The resulting mixture was stirred for 30 minutes under nitrogen, and then potassium hydrogen carbonate (0.959 g, 9.58 mmol) was added. The reaction mixture was stirred for 14 h. The mixture was filtered, and the solid was rinsed with ethyl acetate (10 ml). The filtrate was washed with a saturated aqueous solution of ammonium chloride (10 mL), washed with brine (10 mL), and concentrated. The residue was purified by flash silica gel chromatography using EtOAc/Hexane as the solvent. The fractions containing the product were pooled and concentrated to give the product as an oil (1.15 g, 63% yield) as a mixture of the desired isomer, ethyl 3-(pyridin-2-yl)-4-(trifluoromethyl)isoxazole-5-carboxylate and the undesired isomer, ethyl 3-(pyridine-2-yl)-5-(trifluoromethyl)isoxazole-4-carboxylate in a ratio of approximately 30:1. MS m/e 287.02 (M+H⁺); ¹H NMR (DMSO, 400 MHz) δ 8.73 (d, J=4.0 Hz, 1H), 8.01 (m, 1H), 7.87 (d, J=8.0 Hz, 1H), 7.65 (m, 1H), 4.53 (q, J=8.0 Hz, 2H,), 1.46 (t, J=8.0 Hz, 3H); HPLC (XBridge 5µ C18 4.6×50 mm, 4 mL/min; Solvent A: 10% MeOH/water with 0.2% H₃PO₄; Solvent B: 90% MeOH/water with 0.2% H₃PO₄, gradient with 0-100% B over 4 minutes): 3.57 minutes.

1-C. 3-(Pyridin-2-yl)-4-(trifluoromethyl)isoxazole-5-carboxylic acid

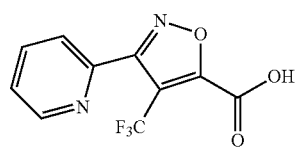

(1-C)

To a solution of ethyl 3-(pyridin-2-yl)-4-(trifluoromethyl)isoxazole-5-carboxylate (511 mg, 1.79 mmol) in methanol (12 mL) and water (3 mL) at room temperature was added lithium hydroxide, hydrate (74.9 mg, 1.79 mmol). The reaction mixture was stirred for 1 hr. A 1N aqueous solution of hydrochloric acid (1.8 mL) was added, and the solvent were removed under reduced pressure to afford 3-(pyridin-2-yl)-4-(trifluoromethyl)isoxazole-5-carboxylic acid+1LiCl (531 mg, 1.767 mmol, 99% yield) as a white solid. The compound had an HPLC ret. time=0.725 min.—Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. LC/MS M⁺¹=258.8. ¹H NMR (400 MHz, CD₃OD) δ ppm 7.59 (dd, J=7.03, 5.02 Hz, 1H), 7.82 (d, J=7.78 Hz, 1H), 8.01 (td, J=7.78, 1.76 Hz, 1H), and 8.73 (d, 1H).

1-D. tert-Butyl 1-(4-(5-(3-(pyridin-2-yl)-4-(trifluoromethyl)isoxazol-5-yl)-1,2,4-oxadiazol-3-yl)benzyl)azetidine-3-carboxylate

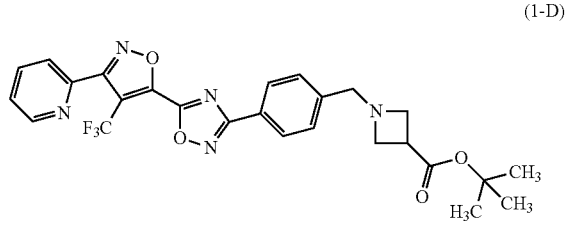 [SMILES: CC(C)(C)OC(=O)C1CN(Cc2ccc(-c3noc(-c4onc(-c5ccccn5)c4C(F)(F)F)n3)cc2)C1]

(1-D)

A mixture of 3-(pyridin-2-yl)-4-(trifluoromethyl)isoxazole-5-carboxylic acid, 1×LiCl (0.030 g, 0.100 mmol), tert-butyl 1-(4-(N'-hydroxycarbamimidoyl)benzyl) azetidine-3-carboxylate, Int. 1 (0.037 g, 0.120 mmol), BOP—Cl (0.031 g, 0.120 mmol), and triethylamine (0.042 mL, 0.300 mmol) in N,N-dimethylformamide (0.5 mL) was stirred at room temperature over the weekend. The reaction mixture was diluted with dichloromethane, washed with a saturated aqueous solution of sodium bicarbonate, and dried over anhydrous sodium sulfate. Concentration followed by purification by flash silica gel chromatography using a 1% mixture of methanol in dichloromethane afforded tert-butyl 1-(4-(5-(3-(pyridin-2-yl)-4-(trifluoromethyl)isoxazol-5-yl)-1,2,4-oxadiazol-3-yl)benzyl)azetidine-3-carboxylate (0.032 g, 0.061 mmol, 61% yield) as a white solid. The compound had an HPLC retention. time=2.74 min.—Column: CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. LC/MS M⁺¹=528.3. ¹H NMR (500 MHz, CD₃OD) δ ppm 3.23-3.30 (m, 1H), 3.40 (t, J=7.56 Hz, 2H), 3.55 (t, J=8.25 Hz, 2H), 3.74 (s, 2H), 7.53 (d, J=8.25 Hz, 2H), 7.62 (ddd, J=7.56, 4.81, 1.10 Hz, 1H), 7.95 (d, J=7.70 Hz, 1H), 8.02-8.07 (m, 1H), 8.16 (d, J=8.25 Hz, 2H), and 8.78 (d, J=4.95 Hz, 1H).

Alternative Preparation of tert-butyl 1-(4-(5-(3-(pyridin-2-yl)-4-(trifluoromethyl)isoxazol-5-yl)-1,2,4-oxadiazol-3-yl)benzyl)azetidine-3-carboxylate (1-D)

1-E. Ethyl 3-(pyridin-2-yl)isoxazole-5-carboxylate

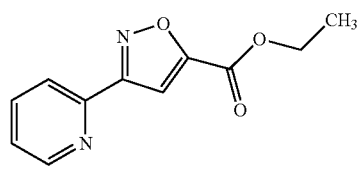

(1-E)

To a suspension of (Z)—N-hydroxypicolinimidoyl chloride (29.7 g, 190 mmol) in dichloromethane (311 mL) in a three neck 1000 ml flask (which was immersed in water) equipped with an addition funnel and thermometer was added the ethyl propiolate (19.3 mL, 190 mmol). The addition funnel was charged with triethylamine (31.7 mL, 228 mmol) in dichloromethane (20 mL), and this solution was slowly added to the reaction mixture drop-wise while maintaining the temperature between 20° C. and 28° C. (by adding ice to the water bath). After the triethylamine was completely added, the water bath was removed, and the reaction mixture was stirred at room temperature for 30 min. The mixture was then partitioned between ethyl acetate (350 mL) and water. The organic layer was collected and washed with brine, the combined aqueous layers were washed with ethyl acetate. The combined organic layers were dried over anhydrous sodium sulfate. Partial concentration under reduced pressure afforded tan crystals which were collected by vacuum filtration and washed with hexane to give the product (14.4 g). The filtrate was concentrated under reduced pressure, and the residue was purified by flash silica gel chromatography using a 20% mixture of ethyl acetate in hexane. The entire product was collected in two batches (one had a trace amount of a slower running spot.) and concentrated. Hexanes were added to the residue, and the product crystallized as colorless prisms (20.1 g). Total product yield: 34.5 g, 158 mmol, 83% yield. The compound had an HPLC ret. time=1.82 min.—Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=218.9 $^1$H NMR (500 MHz, DMSO-$d_6$) δ ppm 1.35 (t, J=7.15 Hz, 3H), 4.41 (q, J=7.15 Hz, 2H), 7.55-7.60 (m, 1H), 7.68 (s, 1H), 8.01 (t, J=7.70 Hz, 1H), 8.10 (d, J=8.25 Hz, 1H), and 8.75 (d, J=4.40 Hz, 1H).

1-F. 5-(3-(Pyridin-2-yl)isoxazol-5-yl)-3-p-tolyl-1,2,4-oxadiazole

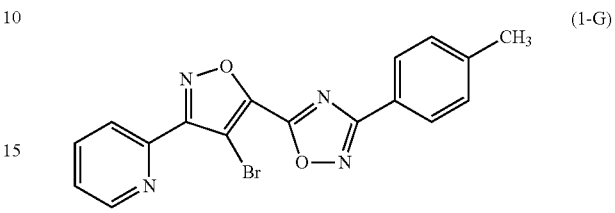

To a solution of ethyl 3-(pyridin-2-yl)isoxazole-5-carboxylate (13.6 g, 62.5 mmol) and (Z)—N'-hydroxy-4-methylbenzimidamide (9.68 g, 62.5 mmol) in N,N-dimethylformamide (210 mL) cooled in an ice-bath was added 60% sodium hydride (6.25 g, 156 mmol) portion-wise. After the addition, the reaction mixture was warmed to room temperature and stirred for 1 h. The reaction mixture was concentrated, water (500 mL) was added, and the mixture was stirred at room temperature for 30 minutes. The solid was collected vacuum filtration, triturated with methanol, and re-collected to give 5-(3-(pyridin-2-yl)isoxazol-5-yl)-3-p-tolyl-1,2,4-oxadiazole (17.8 g, 93% yield) as a solid. The compound had an HPLC retention time=3.86 minutes (YMC-Combi 4.6×50 mm S-5 ODS column) eluting with 10-90% aqueous methanol+0.2% phosphoric acid over a 4 minute gradient. MS: (M+H)=305$^+$. $^1$H NMR (400 MHz, CDCl$_3$) δ ppm 2.46 (s, 3H), 7.35 (d, J=8.28 Hz, 2H), 7.41-7.47 (m, 1H), 7.83-7.91 (m, 2H), 8.09 (d, J=8.28 Hz, 2H), 8.20 (d, J=8.03 Hz, 1H), and 8.76 (d, J=5.02 Hz, 1H).

1-G. 5-(4-Bromo-3-(pyridin-2-yl)isoxazol-5-yl)-3-p-tolyl-1,2,4-oxadiazole

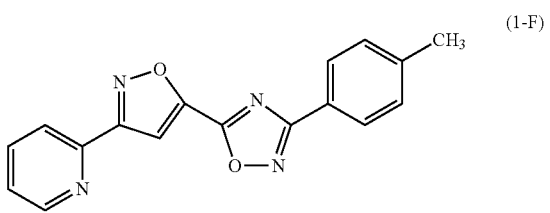 [SMILES: Cc1ccc(-c2noc(-c3cc(-c4ccccn4)no3)n2)cc1]

A solution of 5-(3-(pyridin-2-yl)isoxazol-5-yl)-3-p-tolyl-1,2,4-oxadiazole (655 mg, 2.15 mmol), N-bromosuccinimide (536 mg, 3.01 mmol), and PdOAc$_2$ (97 mg, 0.430 mmol) in acetonitrile (12 mL) was heated to 120° C. via microwave for 30 minutes. The reaction was repeated three additional times on a similar scale, and the contents of each reaction tube were combined and filtered. The solid was collected, triturated with methanol (10 mL), and collected by vacuum filtration to give 5-(4-bromo-3-(pyridin-2-yl)isoxazol-5-yl)-3-p-tolyl-1,2,4-oxadiazole (3.24 g, 87% yield). The compound had an HPLC retention time=3.96 minutes (YMC-Combi 4.6×50 mm S-5 ODS column) eluting with 10-90% aqueous methanol+0.2% phosphoric acid over a 4 minute gradient. MS: (M+H)=385$^+$. $^1$H NMR (400 MHz, CDCl$_3$) δ ppm 2.46 (s, 3H), 7.35 (d, J=8.03 Hz, 2H), 7.49 (ddd, J=7.65, 4.89, 1.00 Hz, 1H), 7.91 (td, J=7.78, 1.76 Hz, 1H), 8.03 (d, J=7.78 Hz, 1H), 8.12 (d, J=8.28 Hz, 2H), and 8.86 (d, J=4.77 Hz, 1H).

1-H. 5-(4-Iodo-3-(pyridin-2-yl)isoxazol-5-yl)-3-p-tolyl-1,2,4-oxadiazole

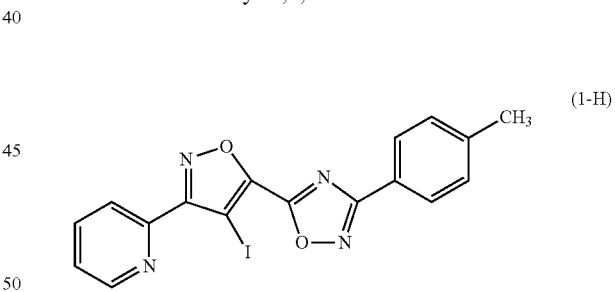

A solution of 5-(3-(pyridin-2-yl)isoxazol-5-yl)-3-p-tolyl-1,2,4-oxadiazole (1.0 g, 3.29 mmol), 1-iodopyrrolidine-2,5-dione (1.11 g, 4.76 mmol), and PdOAc$_2$ (0.148 g, 0.657 mmol) in acetonitrile (14 mL) was heated to 120° C. via microwave for 40 minutes. The reaction was repeated 4 additional times on a similar scale, and the contents of each reaction tube were combined, concentrated, and purified by flash silica gel chromatography (eluting with Hexanes/EtOAc—4/1) to yield 5-(4-iodo-3-(pyridin-2-yl)isoxazol-5-yl)-3-p-tolyl-1,2,4-oxadiazole (5.35 g, 76% yield). The compound had an HPLC retention time=3.81 minutes (YMC-Combi 4.6×50 mm S-5 ODS column) eluting with 10-90% aqueous methanol+0.2% phosphoric acid over a 4 minute gradient. MS: (M+H)=431$^+$. $^1$H NMR (400 MHz, CDCl$_3$) δ ppm 2.46 (s, 3H), 7.36 (d, J=8.03 Hz, 2H), 7.46-7.52 (m, 1H), 7.90 (td, J=7.72, 1.63 Hz, 1H), 8.01 (d, J=7.78 Hz, 1H), 8.12 (d, J=8.28 Hz, 2H), and 8.86 (d, J=4.27 Hz, 1H).

1-I. 5-(3-(Pyridin-2-yl)-4-(trifluoromethyl)isoxazol-5-yl)-3-p-tolyl-1,2,4-oxadiazole

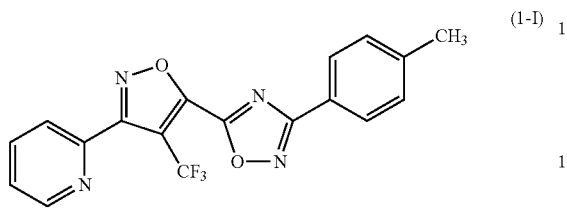

(1-I)

Method A: A solution of 5-(4-bromo-3-(pyridin-2-yl)isoxazol-5-yl)-3-p-tolyl-1,2,4-oxadiazole (600 mg, 1.39 mmol), copper (I) iodide (80 mg, 0.418 mmol), and methyl 2,2-difluoro-2-(fluorosulfonyl)acetate (0.82 mL, 6.41 mmol) in N,N-dimethylformamide (12 mL) and HMPA (1.33 mL) was heated at 85° C. for 25 minutes via microwave. The reaction was repeated 3 additional times on essentially the same scale, and the contents of each reaction tube were combined, diluted with ethyl acetate (150 mL), washed with a 10% aqueous solution of lithium chloride (50 mL), washed with a saturated aqueous solution of ammonium chloride (50 mL), washed with brine, and dried over anhydrous sodium sulfate. Concentration followed by purification by silica gel chromatography (eluting with Hexanes/EtOAc—4/1) afforded 5-(3-(pyridin-2-yl)-4-(trifluoromethyl)isoxazol-5-yl)-3-p-tolyl-1,2,4-oxadiazole (992 mg, 48%). The compound had an HPLC retention time=3.98 minutes (YMC-Combi 4.6×50 mm S-5 ODS column) eluting with 10-90% aqueous methanol+0.2% phosphoric acid over a 4 minute gradient. MS: (M+H)=373$^+$. $^1$H NMR (500 MHz, CDCl$_3$) δ ppm 2.46 (s, 3H), 7.36 (d, J=7.97 Hz, 2H), 7.50 (td, J=5.29, 2.89 Hz, 1H), 7.89-7.94 (m, 2H), 8.10 (d, J=8.25 Hz, 2H), and 8.83 (d, J=4.67 Hz, 1H).

Method B: A solution of 5-(4-iodo-3-(pyridin-2-yl)isoxazol-5-yl)-3-p-tolyl-1,2,4-oxadiazole (1.07 g, 2.49 mmol), copper (I) iodide (0.142 g, 0.746 mmol), and methyl 2,2-difluoro-2-(fluorosulfonyl)acetate (1.49 mL, 11.7 mmol) in N,N-dimethylformamide (13 mL) and HMPA (1.444 mL) was heated at 75° C. for 33 minutes via microwave. The reaction was repeated four additional times on essentially the same scale, and the contents of each reaction were combined, diluted with ethyl acetate (800 mL), washed with a 10% aqueous solution of lithium chloride (2×200 mL), washed with a saturated aqueous solution of ammonium chloride (200 mL), washed with brine (200 mL), and dried over anhydrous sodium sulfate. Concentration followed by purification by silica gel chromatography (eluting with Hexanes/EtOAc—4/1) afforded 5-(3-(pyridin-2-yl)-4-(trifluoromethyl)isoxazol-5-yl)-3-p-tolyl-1,2,4-oxadiazole (1.88 g, 41% yield). The compound had an HPLC retention time=3.98 minutes (YMC-Combi 4.6×50 mm S-5 ODS column) eluting with 10-90% aqueous methanol+0.2% phosphoric acid over a 4 minute gradient. MS: (M+H)=373$^+$. $^1$H NMR (500 MHz, CDCl$_3$) δ ppm 2.46 (s, 3H), 7.36 (d, J=7.97 Hz, 2H), 7.50 (td, J=5.29, 2.89 Hz, 1H), 7.89-7.94 (m, 2H), 8.10 (d, J=8.25 Hz, 2H), and 8.83 (d, J=4.67 Hz, 1H).

1-J. 3-(4-(Bromomethyl)phenyl)-5-(3-(pyridin-2-yl)-4-(trifluoromethyl)isoxazol-5-yl)-1,2,4-oxadiazole

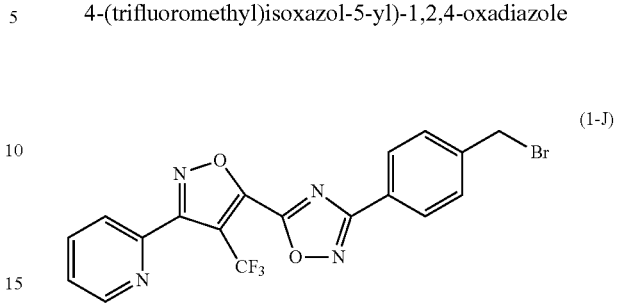

(1-J)

To a solution of 5-(3-(pyridin-2-yl)-4-(trifluoromethyl)isoxazol-5-yl)-3-p-tolyl-1,2,4-oxadiazole (2.69 g, 7.22 mmol) in acetonitrile (50 mL) at 75° C. was added N-bromosuccinimide (2.70 g, 15.2 mmol) followed by AIBN (0.320 g, 1.949 mmol). The reaction mixture was stirred at 75° C. for 2.5 h. The reaction mixture was concentrated, and the crude product was diluted with ethyl acetate (200 mL), washed with a saturated aqueous solution of sodium bicarbonate (50 mL), washed with water (50 mL), washed with brine (50 mL), and dried over anhydrous sodium sulfate. Concentration under reduced pressure gave a crude product which was triturated with methanol. The resulting solid was collected as 3-(4-(bromomethyl)phenyl)-5-(3-(pyridin-2-yl)-4-(trifluoromethyl)isoxazol-5-yl)-1,2,4-oxadiazole (2.524 g, 77% yield). The compound had an HPLC retention time=3.86 minutes (YMC-Combi 4.6×50 mm S-5 ODS column) eluting with 10-90% aqueous methanol+0.2% phosphoric acid over a 4 minute gradient. MS: (M+H)=453$^+$. $^1$H NMR (400 MHz, MeOD) δ ppm 4.66 (s, 2H), 7.62 (dd, J=7.03, 5.27 Hz, 1H), 7.66 (d, J=8.03 Hz, 2H), 7.93-7.98 (m, 1H), 8.01-8.08 (m, 1H), 8.18 (d, J=8.03 Hz, 2H), and 8.79 (d, J=4.77 Hz, 1H).

1-D. Alternate Preparation of tert-butyl 1-(4-(5-(3-(pyridin-2-yl)-4-(trifluoromethyl)-isoxazol-5-yl)-1,2,4-oxadiazol-3-yl)benzyl)azetidine-3-carboxylate

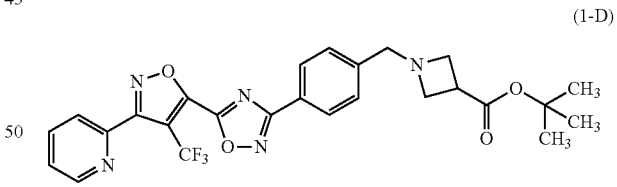

(1-D)

A solution of 3-(4-(bromomethyl)phenyl)-5-(3-(pyridin-2-yl)-4-(trifluoromethyl)-isoxazol-5-yl)-1,2,4-oxadiazole (2.52 g, 5.59 mmol) and tert-butyl azetidine-3-carboxylate, acetic acid (1.82 g, 8.39 mmol) in N,N-dimethylformamide (40 mL) cooled with an ice-water bath was added triethylamine (2.34 mL, 16.8 mmol) drop-wise. The reaction mixture was stirred for 30 minutes, diluted with ethyl acetate (350 mL), washed with a 10% aqueous solution of lithium chloride (2×100 mL), washed with water (100 mL), washed with brine (100 mL), and dried over anhydrous sodium sulfate. Concentration gave a crude product which was triturated with methanol. The resulting solid was collected by vacuum filtration. The filtrate was concentration and purified by silica gel chromatography (eluting with Hexanes/ethyl acetate-4/1) to yield additional product. The material was combined to give tert-butyl 1-(4-(5-(3-(pyridin-2-yl)-4-(trifluoromethyl)isoxazol-5-yl)-1,2,4-oxadiazol-3-yl)benzyl)azetidine-3-carboxylate (2.46 g, 83% yield).

1. Preparation of 1-(4-(5-(3-(pyridin-2-yl)-4-(trifluoromethyl)isoxazol-5-yl)-1,2,4-oxadiazol-3-yl)benzyl)azetidine-3-carboxylic acid A mixture of tert-butyl 1-(4-(5-(3-(pyridin-2-yl)-4-(trifluoromethyl)isoxazol-5-yl)-1,2,4-oxadiazol-3-yl)benzyl)azetidine-3-carboxylate (0.450 g, 0.853 mmol) and trifluoroacetic acid (10.19 mL, 132 mmol) was stirred at room temperature for 60 min. The trifluoroacetic acid was removed under reduced pressure, and the residue was suspended in water (15 mL). The pH was adjusted to approximately 4.5 with a 1N aqueous solution of sodium hydroxide, and the resulting suspension was stirred for 2 h, filtered under reduced pressure, washed with water, and dried well overnight under reduced pressure to give 1-(4-(5-(3-(pyridin-2-yl)-4-(trifluoromethyl)isoxazol-5-yl)-1,2,4-oxadiazol-3-yl)benzyl)azetidine-3-carboxylic acid (0.306 g, 0.641 mmol, 75% yield) as a white solid. The product had an HPLC retention time=2.27 min.—Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=472.4. $^1$H NMR (500 MHz, DMSO-$d_6$) δ ppm 3.21-3.27 (m, 3H), 3.40-3.46 (m, 2H), 3.66 (s, 2H) 7.53 (d, J=8.25 Hz, 2H), 7.66-7.70 (m, 1H), 7.98 (d, J=7.70 Hz, 1H), 8.04-8.12 (m, 3H), and 8.83 (d, 1H).

HPLC purity 99.1/98.8%, ret. time=6.80 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a SunFire C18 3.5 u 4.6×150 mm column. Flow rate was 2 ml/min and UV detection was set to 220/254 nm.).

HPLC purity 98.7/98.7%, ret. time=7.55 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a XBridge Ph 3.5 u 4.6×150 mm column. Flow rate was 2 ml/min and UV detection was set to 220/254 nm.).

Example 2

1-(4-(5-(5-(Pyridin-2-yl)-4-(trifluoromethyl)isoxazol-3-yl)-1,2,4-oxadiazol-3-yl)benzyl)azetidine-3-carboxylic acid (2)

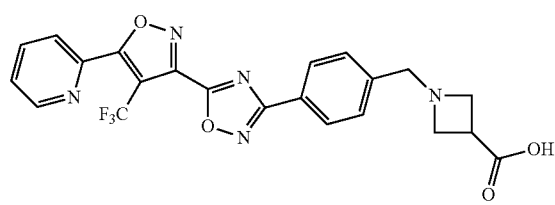

2-A. 5-(Tributylstannyl)isoxazole-3-carboxylate (2-A)

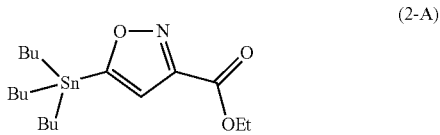

An oven dried 500 mL round bottom flask equipped with a stir bar was cooled under a stream of dry nitrogen. Ethyl chlorooximidoacetate (4.95 g, 32.7 mmol), diethyl ether (100 mL), and tributyl(ethynyl)tin (9.45 mL, 32.7 mmol) were added to give a clear pale yellow solution. Triethylamine (6.83 mL, 49.0 mmol) was added dropwise via syringe. After ~500 µL had been added, the solution became cloudy. After the addition of ~2 mL, the solution began to boil, so a cold water bath was introduced and the rate of addition was slowed. The triethylamine was added slowly over 10 minutes to give a pale yellow suspension which was stirred at room temperature overnight. The solution was cooled using a dry-ice bath, filtered cold, and rinsed with cold diethyl ether. The filtrate was evaporated and placed under high vacuum to afford a pale, amber oil (15 g). The oil was purified by flash chromatography (ISCO, 330 g silica gel, eluting with 5% to 20% ethyl acetate in hexanes). The product fractions were evaporated and placed under high vacuum to afford ethyl 5-(tributylstannyl)isoxazole-3-carboxylate (11 g, 25.3 mmol, 78% yield) as a clear colorless oil. The product had an HPLC retention. Time=4.47 min.—Column: YMC S5 COMBISCREEN® 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=432.12. $^1$H NMR (400 MHz, CDCl$_3$) δ ppm 0.90 (t, J=7.28 Hz, 9H), 1.17-1.62 (m, 21H), 4.45 (q, J=7.03 Hz, 2H), and 6.81 (s, 1H).

2-B. Ethyl 5-(pyridin-2-yl)isoxazole-3-carboxylate (2-B)

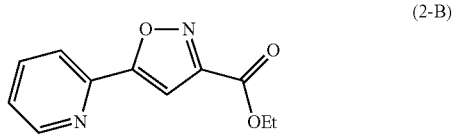 [SMILES: CCOC(=O)c1cc(-c2ccccn2)on1]

A 20 mL BIOTAGE® microwave vial and stir bar were oven dried and cooled under a stream of dry nitrogen. The vial was flushed with argon and charged with dichlorobis(triphenylphosphine)-palladium(II) (96 mg, 0.137 mmol) and dioxane (12 mL) followed by sparging with argon for several minutes. 2-Bromopyridine (0.217 mL, 2.28 mmol), ethyl 5-(tributylstannyl)isoxazole-3-carboxylate (980 mg, 2.28 mmol), and 1-butyl-3-methylimidazolium hexafluorophosphate (0.047 mL, 0.228 mmol) were added and sparging was continued for several minutes. The vial was sealed and processed in a BIOTAGE® microwave at 150° C. for 60 minutes. The solution was cooled, evaporated, and the residue was loaded onto a 120 g Isco silica gel cartridge, which was pre-equilibrated with hexanes, and then eluted with 0-50% EtOAc/Hexanes. The product fractions were evaporated to give a pale yellow oil, which solidified after being placed under high vacuum to afford ethyl 5-(pyridin-2-yl)isoxazole-3-carboxylate (212 mg, 0.972 mmol, 43% yield). The product had an HPLC retention. time=2.48 min.—Column: YMC S5 COMBISCREEN® 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=219.1. $^1$H NMR (400 MHz, chloroform-d) δ ppm 1.42-1.48 (m, 3H), 4.49 (q, J=7.28 Hz, 2H), 7.31 (s, 1H), 7.39 (ddd, J=7.53, 4.89, 1.13 Hz, 1H), 7.87 (td, J=7.78, 1.76 Hz, 1H), 7.96 (d, J=7.78 Hz, 1H), and 8.73 (d, 1H).

2-C. Ethyl 4-bromo-5-(pyridin-2-yl)isoxazole-3-carboxylate

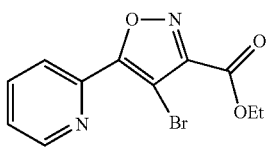

(2-C)

A solution of ethyl 5-(pyridin-2-yl)isoxazole-3-carboxylate (212 mg, 0.972 mmol) and N-bromosuccinimide (432 mg, 2.43 mmol) in trifluoroacetic acid (6 mL) was heated to 150° C. for 30 minutes via microwave. Concentration under reduced pressure afforded a yellow oil which was diluted with ethyl acetate (80 mL), washed with a saturated aqueous solution of sodium bicarbonate (20 mL), washed with brine (20 mL), and dried over anhydrous sodium sulfate. Concentration under reduced pressure followed by purification by flash silica gel chromatography using a 1:3 mixture ethyl acetate and hexane afforded ethyl 4-bromo-5-(pyridin-2-yl)isoxazole-3-carboxylate (0.217 g, 0.672 mmol, 69% yield). The product had an HPLC retention. time=2.65 min.—Column: YMC S5 COMBISCREEN® 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=299.02. $^1$H NMR (400 MHz, CDCl$_3$) δ ppm 1.48 (t, J=7.15 Hz, 3H), 4.52 (q, J=7.28 Hz, 2H), 7.43-7.48 (m, 1H), 7.90 (td, J=7.78, 1.76 Hz, 1H), 8.11 (d, J=8.03 Hz, 1H), and 8.84 (d, 1H).

2-D. Ethyl 5-(pyridin-2-yl)-4-(trifluoromethyl)isoxazole-3-carboxylate

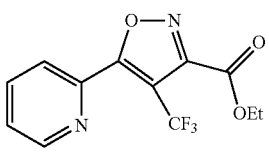

(2-D)

A solution of ethyl 4-bromo-5-(pyridin-2-yl)isoxazole-3-carboxylate (190 mg, 0.640 mmol), copper(I) iodide (36.5 mg, 0.192 mmol), and methyl 2,2-difluoro-2-(fluorosulfonyl)acetate (0.325 mL, 2.56 mmol) in N,N'-dimethylformamide (4 mL) and HMPA (0.444 mL) was stirred at 75° C. for 7 hrs. The reaction mixture was combined with a previous smaller scale reaction (0.084 mmol), diluted with ethyl acetate (80 mL), washed with a 10% aqueous solution of lithium chloride (2×20 mL), washed with a saturated aqueous solution of ammonium chloride (20 mL), washed with brine (20 mL), and dried over anhydrous sodium sulfate. Concentration under reduced pressure followed by purification by flash silica gel chromatography using a 1:4 mixture of ethyl acetate and hexane afforded ethyl 5-(pyridin-2-yl)-4-(trifluoromethyl)isoxazole-3-carboxylate (0.138 g, 99% yield). The product had an HPLC retention. time=2.84 min.—Column: YMC S5 COMBISCREEN® 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=287.12. $^1$H NMR (500 MHz, CDCl$_3$) δ ppm 1.45 (t, J=7.15 Hz, 3H), 4.52 (q, J=7.15 Hz, 2H), 7.51 (ddd, J=7.63, 4.88, 1.24 Hz, 1H), 7.83 (d, J=7.70 Hz, 1H), 7.88-7.94 (m, 1H), and 8.83 (d, J=4.67 Hz, 1H).

2-E. 5-(Pyridin-2-yl)-4-(trifluoromethyl)isoxazole-3-carboxylic acid

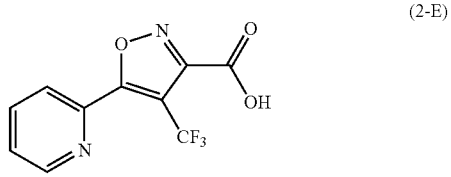 [SMILES: O=C(O)c1noc(-c2ccccn2)c1C(F)(F)F]

(2-E)

A solution of ethyl 5-(pyridin-2-yl)-4-(trifluoromethyl)isoxazole-3-carboxylate (138 mg, 0.482 mmol) and 1N aqueous sodium hydroxide (579 μL, 0.579 mmol) in ethanol (4.5 mL) was stirred at room temperature for 30 min. The reaction mixture was concentrated under reduced pressure, and the residue was diluted with water (0.5 mL) and acidified with a 1N aqueous solution of hydrochloric acid to a pH of ~3.0. The solution was extracted with ethyl acetate (3×2 mL). The organic layer was washed with water (1 mL), washed with brine (1 mL), and dried over anhydrous sodium sulfate. Concentration under reduced pressure afforded 5-(pyridin-2-yl)-4-(trifluoromethyl)isoxazole-3-carboxylic acid (0.093, 0.361 mmol, 75% yield). The product had an HPLC retention. time=1.57 min.—Column: YMC S5 COMBISCREEN® 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=259.0. $^1$H NMR (400 MHz, CD$_3$OD) δ ppm 7.60-7.65 (m, 2H), 7.92 (d, J=8.03 Hz, 2H), 8.02-8.09 (m, 2H), and 8.78 (d, 2H).

2-F. 5-(Pyridin-2-yl)-4-(trifluoromethyl)isoxazole-3-carbonyl fluoride

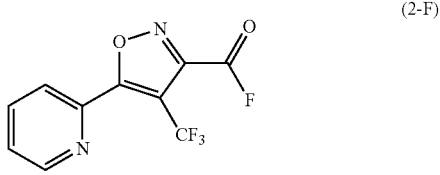 [SMILES: O=C(F)c1noc(-c2ccccn2)c1C(F)(F)F]

(2-F)

To a solution of 5-(pyridin-2-yl)-4-(trifluoromethyl)isoxazole-3-carboxylic acid (54.3 mg, 0.210 mmol) and pyridine (0.037 mL, 0.463 mmol) in dichloromethane (2 mL) was added cyanuric fluoride (0.021 mL, 0.252 mmol). The reaction mixture was stirred at room temperature for 2 hrs., diluted with dichloromethane (2 mL), and washed with ice water (1 mL). The aqueous layer was extracted with dichloromethane (2×1 mL), and the combined organic layers were washed with brine (1 mL) and dried over anhydrous sodium sulfate. Concentration under reduced pressure afforded 5-(pyridin-2-yl)-4-(trifluoromethyl)isoxazole-3-carbonyl fluoride (0.048 g, 0.185 mmol, 88% yield). The product had an HPLC retention. time=2.50 min. (The product reacted readily with methanol and a small portion was characterized as the methyl ester)—Column: YMC S5 COMBISCREEN® 4.6×50 mm (4 min.); Solvent A=10% MeOH, 90% H$_2$O, 0.1% TFA; Solvent B=90% MeOH, 10% H$_2$O, 0.1% TFA.

2-G. tert-Butyl 1-(4-(5-(5-(pyridin-2-yl)-4-(trifluoromethyl)isoxazol-3-yl)-1,2,4-oxadiazol-3-yl)benzyl)azetidine-3-carboxylate

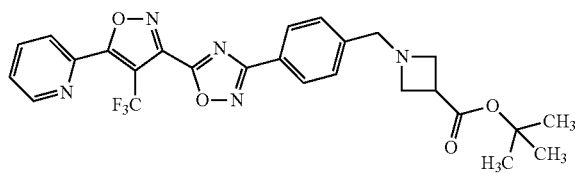

(2-G)

To a solution of 5-(pyridin-2-yl)-4-(trifluoromethyl)isoxazole-3-carbonyl fluoride (48 mg, 0.185 mmol) and tert-butyl 1-(4-(N'-hydroxycarbamimidoyl)benzyl)azetidine-3-carboxylate, Int. 1 (56.3 mg, 0.185 mmol) in dichloromethane (2 mL) was added pyridine (37.3 μL, 0.461 mmol). The reaction mixture was stirred at room temperature for 16 hrs. The reaction mixture was then concentrated under reduced pressure, and the residue was diluted with ethyl acetate (3 mL), washed with water (1 mL), washed with a saturated aqueous solution of sodium bicarbonate (1 mL), washed with brine (1 mL), and dried over anhydrous sodium sulfate. Concentration under reduced pressure resulted in the crude mixture which was dissolved in acetonitrile (2 mL). A 1.0M solution of tetrabutylammonium fluoride in tetrahydrofuran (369 μL, 0.369 mmol) was added, and the solution was stirred at room temperature for 30 min. The reaction mixture was diluted with ethyl acetate (30 mL), washed with water (10 mL), washed with a saturated aqueous solution of sodium bicarbonate (10 mL), washed with brine (10 mL), and dried over anhydrous sodium sulfate. Concentration under reduced pressure followed by purification by preparative HPLC afforded tert-butyl-1-(4-(5-(5-(pyridin-2-yl)-4-(trifluoromethyl)isoxazol-3-yl)-1,2,4-oxadiazol-3-yl)benzyl)azetidine-3-carboxylate, which was used in the next step without any further purification. The product had an HPLC retention time=2.97 min.—Column: YMC S5 COMBISCREEN® 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=528.3.

2. Preparation of 1-(4-(5-(5-(pyridin-2-yl)-4-(trifluoromethyl)isoxazol-3-yl)-1,2,4-oxadiazol-3-yl)benzyl)-azetidine-3-carboxylic acid To a solution of tert-butyl-1-(4-(5-(5-(pyridin-2-yl)-4-(trifluoromethyl)isoxazol-3-yl)-1,2,4-oxadiazol-3-yl)benzyl)azetidine-3-carboxylate (previous reaction) in dichloromethane (0.5 mL) was added trifluoroacetic acid (0.5 mL), and the mixture was stirred at room temperature for 30 min. The reaction mixture was concentrated under reduced pressure, and the residue was treated with triethylamine and re-concentrated. The product mixture was purified by flash silica gel chromatography using a mixture of methanol, dichloromethane, and ammonium hydroxide (10:90:0-10:90:1-15:85:1-20:80:1) to give 1-(4-(5-(5-(pyridin-2-yl)-4-(trifluoromethyl)isoxazol-3-yl)-1,2,4-oxadiazol-3-yl)benzyl)azetidine-3-carboxylic acid (0.007 g, 0.015 mmol) as an off-white solid. The product had an HPLC retention time=2.33 min.—Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=472.0. $^1$H NMR (500 MHz, methanol-d$_3$) δ ppm 3.50 (quin, J=8.25 Hz, 1H), 4.21-4.29 (m, 4H), 4.46 (s, 2H), 7.66-7.71 (m, 3H), 8.02-8.05 (m, 1H), 8.08-8.13 (m, 1H), 8.28 (d, J=8.25 Hz, 2H), and 8.83-8.85 (m, 1H).

HPLC purity 99.5/99.6%, ret. time=6.56 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a SunFire C18 3.5 u 4.6×150 mm column. Flow rate was 2 ml/min and UV detection was set to 220/254 nm.).

HPLC purity 99.5/99.7%, ret. time=7.23 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a XBridge Ph 3.5 u 4.6×150 mm column. Flow rate was 2 ml/min and UV detection was set to 220/254 nm.).

Example 3

1-(4-(5-(4-Propyl-5-(pyridin-2-yl)isoxazol-3-yl)-1,2,4-oxadiazol-3-yl)benzyl)azetidine-3-carboxylic acid, 2,2,2-trifluoroacetic acid salt

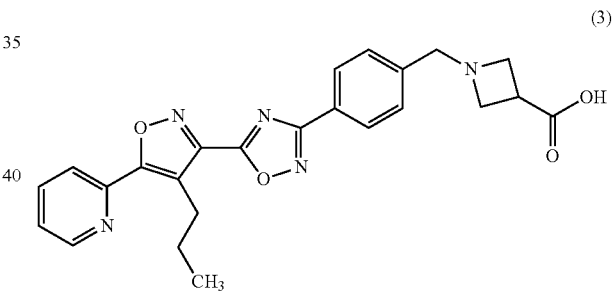

(3)

3-A. 2-(Pent-1-ynyl)pyridine

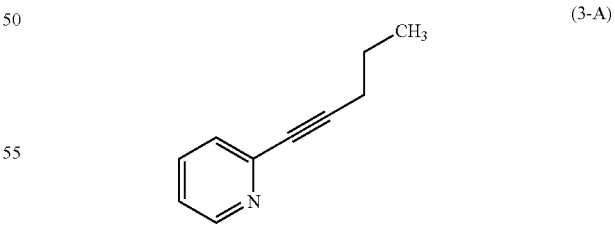

(3-A)

To a degassed solution of 2-iodopyridine (0.519 mL, 4.88 mmol), bis(triphenylphosphine)palladium(II) chloride (0.205 g, 0.293 mmol), copper(I) iodide (0.046 g, 0.244 mmol), and diisopropylamine (2.78 mL, 19.5 mmol) in N,N-dimethylformamide (20 mL) was added 1-pentyne (0.721 mL, 7.32 mmol). The reaction was heated to 85° C. for 3 hrs. The reaction mixture was cooled to room temperature, diluted with ethyl acetate (150 mL), washed with a 10% aqueous solution of lithium chloride (2×100 mL), washed with a 2M aqueous solution of ammonium hydroxide (100 mL), washed with brine (100 mL), and dried over anhydrous sodium sulfate. Concentration followed by purification by silica gel chromatography with hexanes/ethyl acetate (3/2) afforded 2-(pent-1-ynyl)pyridine (636 mg, 4.31 mmol). The compound had an HPLC retention time=0.982 min.—Column: YMC S5 COMBISCREEN® 4.6×50 mm; Gradient time: 4 min; Flow rate=4 ml/min; Solvent A=10% MeOH—90% Water—0.2% $H_3PO_4$; Solvent B=90% MeOH—10% water—0.2% $H_3PO_4$; Start % B=0; Final % B=100. LC-MS: $M^{+1}$=146.3. $^1$H NMR (400 MHz, $CDCl_3$) δ ppm 1.06 (t, 3H), 1.67 (dt, J=7.23 Hz, 2H), 2.43 (t, J=7.15 Hz, 2H), 7.18 (ddd, J=7.65, 4.89, 1.00 Hz, 1H), 7.38 (d, J=7.78 Hz, 1H), 7.62 (td, J=7.72, 1.88 Hz, 1H), and 8.55 (d, J=4.27 Hz, 1H).

3-B. Methyl 4-propyl-5-(pyridin-2-yl)isoxazole-3-carboxylate

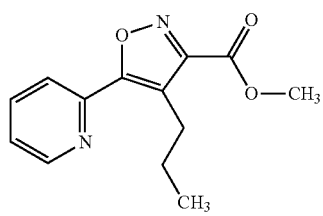

(3-B)

A solution of 2-(pent-1-ynyl)pyridine (150 mg, 1.03 mmol), dimethyl nitromalonate (0.35 mL, 2.58 mmol), and 1-butyl-3-methylimidazolium hexafluorophosphate (0.021 mL, 0.103 mmol) in toluene (3 mL) was heated to 170° C. for 120 minutes under microwave. The reaction mixture was concentrated to yield a crude product which was purified by silica gel chromatography with hexanes/ethyl acetate (10/1) to afford methyl 4-propyl-5-(pyridine-2-yl)isoxazole-3-carboxylate (14.3 mg, 0.052 mmol). The compound had an HPLC retention time=3.05 min.—Column: YMC S5 COMBISCREEN® 4.6×50 mm; Gradient time: 4 min; Flow rate=4 ml/min; Solvent A=10% MeOH—90% Water—0.2% $H_3PO_4$; Solvent B=90% MeOH—10% water—0.2% $H_3PO_4$; Start % B=0; Final % B=100. LC-MS: $M^{+1}$=247.1. $^1$H NMR (500 MHz, $CDCl_3$) δ ppm 0.97 (t, 3H), 1.66 (sxt, J=7.48 Hz, 2H), 3.15-3.20 (m, 2H), 4.01 (s, 3H), 7.33 (ddd, J=7.56, 4.81, 1.10 Hz, 1H), 7.83 (td, J=7.77, 1.79 Hz, 1H), 7.91 (d, J=7.97 Hz, 1H), and 8.72 (d, J=4.12 Hz, 1H).

3-C. 4-Propyl-5-(pyridin-2-yl)isoxazole-3-carboxylic acid

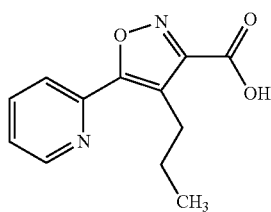

(3-C)

A solution of methyl 4-propyl-5-(pyridin-2-yl)isoxazole-3-carboxylate (14.3 mg, 0.058 mmol) and 1N aqueous sodium hydroxide (87 µL, 0.087 mmol) in methanol (1 mL) was heated at 100° C. for 10 minutes under microwave. The reaction mixture was concentrated to yield 4-propyl-5-(pyridin-2-yl)isoxazole-3-carboxylic acid, sodium salt (16 mg). The material was used without further purification. The compound had an HPLC retention time=2.60 min.—Column: YMC S5 COMBISCREEN® 4.6×50 mm; Gradient time: 4 min; Flow rate=4 ml/min; Solvent A=10% MeOH—90% Water—0.2% $H_3PO_4$; Solvent B=90% MeOH—10% water—0.2% $H_3PO_4$; Start % B=0; Final % B=100. LC-MS: $M^{+1}$=233.1.

3. Preparation of 1-(4-(5-(4-propyl-5-(pyridin-2-yl)isoxazol-3-yl)-1,2,4-oxadiazol-3-yl)benzyl)azetidine-3-carboxylic acid, 2,2,2-trifluoroacetic acid salt A solution of 4-propyl-5-(pyridin-2-yl)isoxazole-3-carboxylic acid, sodium salt (13.5 mg, approx 0.053 mmol), HOBt (16.0 mg, 0.105 mmol), and diisopropylethylamine (0.041 mL, 0.233 mmol) in acetonitrile (1 mL) was added EDC (26.1 mg, 0.136 mmol) and tert-butyl 1-(4-(N'-hydroxycarbamimidoyl)benzyl)azetidine-3-carboxylate, Int. 1 (17.8 mg, 0.058 mmol). The reaction mixture was stirred at 80° C. for 2 h, cooled to room temperature, and concentrated to yield the crude product. The residue was dissolved in ethyl acetate (3 mL), washed with a saturated aqueous solution of sodium bicarbonate (1 mL), washed with water (1 mL), washed with brine (1 mL), and dried over anhydrous sodium sulfate. Concentration followed by purification by preparative HPLC afforded tert-butyl 1-(4-(5-(4-propyl-5-(pyridin-2-yl)isoxazol-3-yl)-1,2,4-oxadiazol-3-yl)benzyl)azetidine-3-carboxylate. [Prep HPLC: Column: PHENOMENEX® S10 30×100 mm; Gradient time: 10 min; Flow rate=40 ml/min; Solvent A=10% MeOH—90% Water—0.1% TFA; Solvent B=90% MeOH—10% water—0.1% TFA; Start % B=20; Final % B=100.]

A solution of tert-butyl 1-(4-(5-(4-propyl-5-(pyridin-2-yl)isoxazol-3-yl)-1,2,4-oxadiazol-3-yl)benzyl)azetidine-3-carboxylate in dichloromethane (0.5 mL) and trifluoroacetic acid (0.5 mL) was stirred at room temperature for 30 minutes. The reaction mixture was concentrated to yield 1-(4-(5-(4-propyl-5-(pyridin-2-yl)isoxazol-3-yl)-1,2,4-oxadiazol-3-yl)benzyl)azetidine-3-carboxylic acid trifluoroacetic acid salt (17.4 mg). The compound had an HPLC retention time=7.75 min.—Column: Xbridge Ph 3.5 u 4.6×150 mm; Gradient time: 12 min, hold for 3 minutes; Flow rate=2 ml/min; Solvent A=5% MeCN—95% Water—0.05% TFA; Solvent B=95% MeCN—5% water—0.05% TFA; Start % B=10; Final % B=100. LC-MS: $M^{+1}$=446$^+$. $^1$H NMR (500 MHz, MeOD) δ ppm 1.04 (t, 3H), 1.73-1.83 (m, 2H), 3.34-3.40 (m, 2H), 3.73 (t, J=8.25 Hz, 1H), 4.39 (d, J=7.42 Hz, 4H), 4.54 (s, 2H), 7.51 (ddd, J=6.74, 4.67, 2.06 Hz, 1H), 7.70 (d, J=8.25 Hz, 2H), 7.98-8.06 (m, 2H), 8.30 (d, J=8.25 Hz, 2H), and 8.78 (d, J=4.40 Hz, 1H).

Example 4

1-(4-(5-(4-Isopropyl-5-(pyridin-2-yl)isoxazol-3-yl)-1,2,4-oxadiazol-3-yl)benzyl)azetidine-3-carboxylate, 2,2,2-trifluoroacetic acid salt

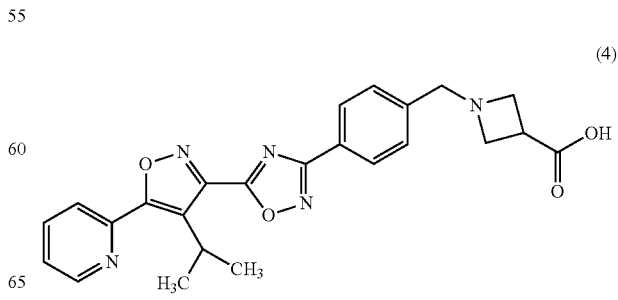

(4)

4-A. 2-(3-Methylbut-1-ynyl)pyridine

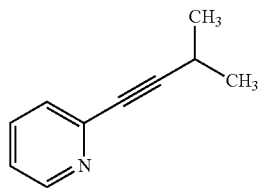

(4-A)

To a degassed solution of 2-bromopyridine (0.604 mL, 6.33 mmol), bis(triphenylphosphine)palladium(II) chloride (0.267 g, 0.380 mmol), copper (I) iodide (0.060 g, 0.316 mmol), and diisopropyldiethylamine (3.61 mL, 25.3 mmol) in N,N-dimethylformamide (20 mL) was added 3-methylbut-1-yne (0.647 g, 9.49 mmol). The reaction mixture was heated to 85° C. for 16 h, cooled to room temperature, and diluted with ethyl acetate (150 mL). The mixture was washed with a 10% aqueous solution of lithium chloride (2×100 mL), washed with a 2M aqueous solution of ammonium hydroxide (100 mL), washed with brine, and dried over anhydrous sodium sulfate. Concentration followed by purification by silica gel chromatography with hexanes/ethyl acetate (3/2) afforded (3-methylbut-1-ynyl)pyridine (696 mg, 4.65 mmol, 73% yield). The compound had an HPLC retention time=1.02 min.—Column: YMC COMBISCREEN® ODS-A 4.6×50 mm S-5; Gradient time: 4 min; Flow rate=4 ml/min; Solvent A=10% MeOH—90% Water—0.1% TFA; Solvent B=90% MeOH—10% water—0.1% TFA. LC-MS: $M^{+1}$=146.32. $^1$H NMR (400 MHz, CDCl$_3$) δ ppm 1.29 (s, 3H), 1.30 (s, 3H), 2.82 (dt, J=13.80, 6.90 Hz, 1H), 7.18 (dd, J=7.65, 4.89 Hz, 1H), 7.37 (d, J=7.78 Hz, 1H), 7.61 (td, J=7.72, 1.13 Hz, 1H), and 8.55 (d, J=4.77 Hz, 1H).

4-B. Methyl 4-isopropyl-5-(pyridin-2-yl)isoxazole-3-carboxylate

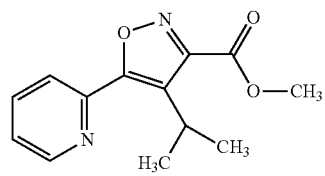

(4-B)

A solution of (3-methylbut-1-ynyl)pyridine (170 mg, 1.17 mmol), dimethyl nitromalonate (0.395 mL, 2.93 mmol), and 1-butyl-3-methylimidazolium hexafluorophosphate (0.024 mL, 0.117 mmol) in toluene (7 mL) was heated to 170° C. for 120 minutes under microwave. The reaction mixture was concentrated and purified by silica gel chromatography with hexanes/ethyl acetate (10/1) to afford methyl 4-isopropyl-5-(pyridin-2-yl)isoxazole-3-carboxylate (11 mg, 0.033 mmol, 2.8% yield). The compound had an HPLC retention time=2.96 min.—Column: YMC S5 COMBISCREEN® 4.6×50 mm; Gradient time: 4 min; Flow rate=4 ml/min; Solvent A=10% MeOH—90% Water—0.2% H$_3$PO$_4$; Solvent B=90% MeOH—10% water—0.2% H$_3$PO$_4$; Start % B=0; Final % B=100. LC-MS: $M^{+1}$=247.15. $^1$H NMR (400 MHz, CDCl$_3$) δ ppm 1.36 (s, 3H), 1.38 (s, 3H), 4.02 (s, 3H), 4.03-4.10 (m, 1H), 7.33-7.38 (m, 1H), 7.80-7.90 (m, 2H), and 8.72-8.76 (m, 1H).

4-C. 4-Isopropyl-5-(pyridin-2-yl)isoxazole-3-carboxylic acid

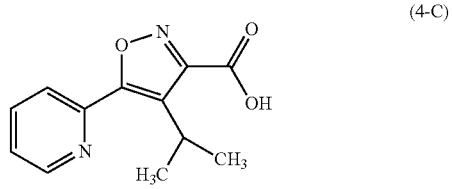 [SMILES: CC(C)c1c(C(=O)O)noc1-c1ccccn1]

(4-C)

A solution of methyl 4-isopropyl-5-(pyridin-2-yl)isoxazole-3-carboxylate (11 mg, 0.045 mmol) and 1N aqueous sodium hydroxide (67 µL, 0.067 mmol) in methanol (1 mL) was heated at 80° C. for 30 minutes under microwave. The reaction mixture was concentrated to yield 4-isopropyl-5-(pyridin-2-yl)isoxazole-3-carboxylic acid, sodium salt (10.4 mg). The material was used without further purification. The compound had an HPLC retention time=2.96 min.—Column: YMC S5 COMBISCREEN® 4.6×50 mm; Gradient time: 4 min; Flow rate=4 ml/min; Solvent A=10% MeOH—90% Water—0.2% H$_3$PO$_4$; Solvent B=90% MeOH—10% water—0.2% H$_3$PO$_4$; Start % B=0; Final % B=100. %). LC-MS: $M^{+1}$=233.1.

4. Preparation of 1-(4-(5-(4-isopropyl-5-(pyridin-2-yl)isoxazol-3-yl)-1,2,4-oxadiazol-3-yl)benzyl)azetidine-3-carboxylate, 2,2,2-trifluoroacetic acid salt To a solution of 4-isopropyl-5-(pyridin-2-yl)isoxazole-3-carboxylic acid salt (10.4 mg, approx. 0.045 mmol), HOBt (12.34 mg, 0.081 mmol), and diisopropylethylamine (0.031 mL, 0.179 mmol) in acetonitrile (1 mL) was added EDC (20.2 mg, 0.105 mmol) and tert-butyl 1-(4-(N'-hydroxycarbamimidoyl)benzyl)azetidine-3-carboxylate, Int. 1 (13.68 mg, 0.045 mmol). The reaction mixture was stirred at 80° C. for 5 h. The reaction mixture was concentrated, and the residue was diluted with ethyl acetate (3 mL), washed with a saturated aqueous solution of sodium bicarbonate (1 mL), washed with water (1 mL), washed with brine (1 mL), and dried over anhydrous sodium sulfate. Concentration followed by purification on a preparative TLC plate with ethyl acetate afforded tert-butyl 1-(4-(5-(4-isopropyl-5-(pyridin-2-yl)isoxazol-3-yl)-1,2,4-oxadiazol-3-yl)benzyl)azetidine-3-carboxylate.

To a solution of the tert-butyl 1-(4-(5-(4-isopropyl-5-(pyridin-2-yl)isoxazol-3-yl)-1,2,4-oxadiazol-3-yl)benzyl)azetidine-3-carboxylate in dichloromethane (0.5 mL) was added trifluoroacetic acid (0.5 mL), and the reaction mixture was stirred at room temperature for 30 minutes. The reaction mixture was concentrated and purified by preparative HPLC [Prep HPLC: Column: PHENOMENEX® S10 30×100 mm; Gradient time: 10 min; Flow rate=40 ml/min; Solvent A=10% MeOH—90% Water—0.1% TFA; Solvent B=90% MeOH—10% water—0.1% TFA; Start % B=20; Final % B=100.] to yield 1-(4-(5-(4-isopropyl-5-(pyridin-2-yl)isoxazol-3-yl)-1,2,4-oxadiazol-3-yl)benzyl)azetidine-3-carboxylate, trifluoroacetic acid salt (2.03 mg, 3.47 mmol, 7.8%). The compound had an HPLC retention time=7.58 min.—Column: Xbridge Ph 3.5 u 4.6×150 mm; Gradient time: 12 min, hold for 3 minutes; Flow rate=2 ml/min; Solvent A=5% MeCN—95% Water—0.05% TFA; Solvent B=95% MeCN—5% water—0.05% TFA; Start % B=10; Final % B=100. LC-MS: M$^{+1}$=446.3. $^1$H NMR (500 MHz, MeOD) δ ppm 1.44 (s, 3H), 1.46 (s, 3H), 3.68-3.76 (m, 1H), 4.19 (quin, J=7.15 Hz, 1H), 4.37-4.42 (m, 4H), 4.54 (s, 2H), 7.53 (ddd, J=7.49, 4.74, 1.24 Hz, 1H), 7.70 (d, J=8.25 Hz, 2H), 7.96-8.00 (m, 1H), 8.00-8.05 (m, 1H), 8.30 (d, J=8.25 Hz, 2H), and 8.79 (d, J=4.67 Hz, 1H).

Example 5

1-(4-(5-(4-Ethyl-5-(pyridin-2-yl)isoxazol-3-yl)-1,2,4-oxadiazol-3-yl)benzyl)-azetidine-3-carboxylic acid, 2,2,2-trifluoroacetic acid salt

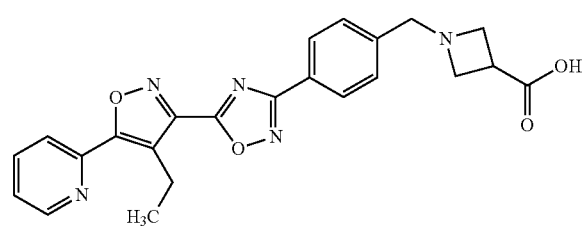

(5)

5-A. Ethyl 5-(pyridin-2-yl)-4-vinylisoxazole-3-carboxylate

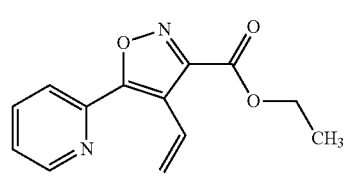

(5-A)

A solution of ethyl 4-bromo-5-(pyridin-2-yl)isoxazole-3-carboxylate (2-C) (170 mg, 0.572 mmol), tributyl(vinyl)tin (0.504 mL, 1.72 mmol), dichlorobis(triphenylphosphine)-palladium(II) (24.1 mg, 0.034 mmol), and 1-butyl-3-methylimidazolium hexafluorophosphate (0.012 mL, 0.057 mmol) in dioxane (3 mL) was heated to 170° C. via microwave for 120 minutes. The reaction mixture was diluted with ethyl acetate (50 mL), washed with water (10 mL), washed with brine (10 mL), and dried over anhydrous sodium sulfate. Concentration gave a crude product which was purified by silica gel chromatography with hexanes/ethyl acetate (4/1) to give ethyl 5-(pyridin-2-yl)-4-vinylisoxazole-3-carboxylate (60 mg, 2.37 mmol, 41% yield). The compound had an HPLC retention time=2.80 min.—Column: YMC S5 COMBISCREEN® 4.6×50 mm; Gradient time: 4 min; Flow rate=4 ml/min; Solvent A=10% MeOH—90% Water—0.2% H$_3$PO$_4$; Solvent B=90% MeOH—10% water—0.2% H$_3$PO$_4$; Start % B=0; Final % B=100. LC-MS: M$^{+1}$=245.2. $^1$H NMR (400 MHz, MeOD) δ ppm 1.42 (t, 3H), 4.47 (q, J=7.19 Hz, 2H), 5.49 (dd, J=11.80, 1.25 Hz, 1H), 5.85 (dd, J=18.07, 1.51 Hz, 1H), 7.26 (dd, J=18.07, 11.80 Hz, 1H), 7.51 (ddd, J=7.03, 5.02, 1.76 Hz, 1H), 7.93-8.02 (m, 2H), and 8.72-8.75 (m, 1H).

5-B. Ethyl 4-ethyl-5-(pyridin-2-yl)isoxazole-3-carboxylate

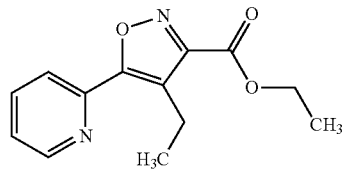

(5-B)

A solution of ethyl 5-(pyridin-2-yl)-4-vinylisoxazole-3-carboxylate (40 mg, 0.164 mmol) and Pd/C (3.49 mg, 0.033 mmol) in ethanol (3 mL) was placed on Parr Shaker under hydrogen (45 psi) for 5 h. Filtration to remove the catalyst followed by concentration under reduced pressure afforded ethyl 4-ethyl-5-(pyridin-2-yl)isoxazole-3-carboxylate (36.1 mg, 0.147 mmol, 90% yield). The compound had an HPLC retention time=3.13 min.—Column: YMC S5 COMBISCREEN® 4.6×50 mm; Gradient time: 4 min; Flow rate=4 ml/min; Solvent A=10% MeOH—90% Water—0.2% H$_3$PO$_4$; Solvent B=90% MeOH—10% water—0.2% H$_3$PO$_4$; Start % B=0; Final % B=100. LC-MS: M$^{+1}$ 247$^+$. $^1$H NMR (400 MHz, MeOD) δ ppm 1.23 (t, 3H), 1.43 (t, J=7.15 Hz, 3H), 3.17 (q, J=7.53 Hz, 2H), 4.46 (q, J=7.28 Hz, 2H), 7.46 (ddd, J=7.03, 5.14, 1.63 Hz, 1H), 7.90-8.01 (m, 2H), and 8.73 (dt, J=4.77, 1.38 Hz, 1H).

5-C. 4-Ethyl-5-(pyridin-2-yl)isoxazole-3-carboxylic acid

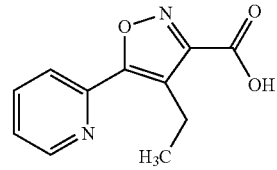

(5-C)

A solution of ethyl 4-ethyl-5-(pyridin-2-yl)isoxazole-3-carboxylate (24.6 mg, 0.100 mmol) and 1N aqueous sodium hydroxide (150 μL, 0.150 mmol) in methanol (1 mL) was heated at 80° C. for 20 minutes. The reaction mixture was concentrated to yield 4-ethyl-5-(pyridin-2-yl)isoxazole-3-carboxylic acid, sodium salt (26 mg). The compound had an HPLC retention time=3.13 min.—Column: YMC S5 COMBISCREEN® 4.6×50 mm; Gradient time: 4 min; Flow rate=4 ml/min; Solvent A=10% MeOH—90% Water—0.2% H$_3$PO$_4$; Solvent B=90% MeOH—10% water—0.2% H$_3$PO$_4$; Start % B=0; Final % B=100. LC-MS: M$^{+1}$=219.25.

5. Preparation of 1-(4-(5-(4-ethyl-5-(pyridine-2-yl)isoxazol-3-yl)-1,2,4-oxadiazol-3-yl)benzyl)azetidine-3-carboxylic acid, 2,2,2-trifluoroacetic acid salt To a solution of 4-ethyl-5-(pyridin-2-yl)isoxazole-3-carboxylic acid, sodium salt (22 mg), HOBt (27.8 mg, 0.181 mmol), and diisopropylethylamine (0.070 mL, 0.403 mmol) in acetonitrile (1 mL) was added EDC (45.4 mg, 0.237 mmol)

and tert-butyl 1-(4-(N'-hydroxycarbamimidoyl)benzyl)azetidine-3-carboxylate, Int. 1 (30.8 mg, 0.101 mmol). The reaction mixture was stirred at 80° C. for 4 h. and then concentrated under reduced pressure. The residue was diluted with ethyl acetate (3 mL), washed with a saturated aqueous solution of sodium bicarbonate, washed with water (1 mL), washed with brine (1 mL), and dried over anhydrous sodium sulfate. Concentration followed by purification by preparative HPLC [Prep HPLC: Column: PHENOMENEX® S10 30×100 mm; Gradient time: 10 min; Flow rate=40 ml/min; Solvent A=10% MeOH—90% Water—0.1% TFA; Solvent B=90% MeOH—10% water—0.1% TFA; Start % B=20; Final % B=100.] afforded tert-butyl 1-(4-(5-(4-ethyl-5-(pyridin-2-yl)isoxazol-3-yl)-1,2,4-oxadiazol-3-yl)benzyl)azetidine-3-carboxylate.

A solution of tert-butyl 1-(4-(5-(4-ethyl-5-(pyridin-2-yl)isoxazol-3-yl)-1,2,4-oxadiazol-3-yl)benzyl)azetidine-3-carboxylate in dichloromethane (0.5 mL) and trifluoroacetic acid (0.5 mL) was stirred at room temperature for 30 minutes. The reaction mixture was concentrated to give 1-(4-(5-(4-ethyl-5-(pyridin-2-yl)isoxazol-3-yl)-1,2,4-oxadiazol-3-yl)benzyl)azetidine-3-carboxylic acid, trifluoroacetic acid salt (22.9 mg, 0.042 mmol). The compound had an HPLC retention time=7.33 min.—Column: Xbridge Ph 3.5 u 4.6×150 mm; Gradient time: 12 min, hold for 3 minutes; Flow rate=2 ml/min; Solvent A=5% MeCN—95% Water—0.05% TFA; Solvent B=95% MeCN—5% water—0.05% TFA; Start % B=10; Final % B=100. LC-MS: $M^{+1}$=432.3. $^1$H NMR (400 MHz, MeOD) δ ppm 1.36 (t, 3H), 3.41 (q, J=7.53 Hz, 2H), 3.72 (quin, J=8.34 Hz, 1H), 4.35-4.45 (m, 4H), 4.54 (s, 2H), 7.51 (ddd, J=6.15, 4.77, 2.64 Hz, 1H), 7.70 (d, J=8.53 Hz, 2H), 7.99-8.06 (m, 2H), 8.31 (d, J=8.28 Hz, 2H), and 8.78 (ddd, J=4.64, 1.51, 1.38 Hz, 1H).

Example 6

1-(4-(5-(4-Propyl-3-(pyridin-2-yl)isoxazol-5-yl)-1,2,4-oxadiazol-3-yl)benzyl)-azetidine-3-carboxylic acid, 2,2,2-trifluoroacetic acid salt

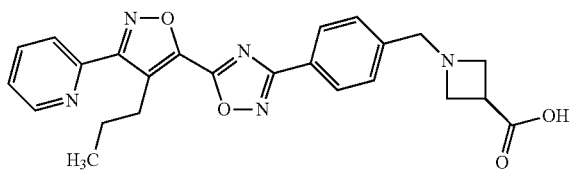

(6)

6-A. (E,Z)-Ethyl 2-bromohex-2-enoate

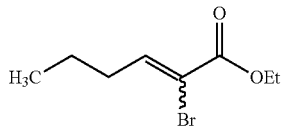

(6-A)

To a suspension of sodium hydride, 60% (0.800 g, 20.0 mmol) in tetrahydrofuran (40 mL), cooled in an adiabatic cooling bath, was added portion-wise over 15 minutes triethylphosphonoacetate (4.00 mL, 20 mmol). The reaction mixture was allowed to stir at room temperature for 45 minutes. At this time, bromine (1.03 mL, 20.0 mmol) was added dropwise over 15 minutes. The orange color discharged immediately after each drop hit the reaction; however, when the addition was complete a light orange color persisted and the reaction mixture was a light orange suspension. This suspension was warmed to 40° C. for 10 minutes and was then allowed to stir at room temperature for 1 h. The reaction mixture was cooled to 10° C. Sodium hydride, 60% (0.800 g, 20.0 mmol) was added in one portion, and the reaction mixture was allowed to warm to room temperature and stir for 45 minutes. Gas evolution was observed. Butyraldehyde (1.80 mL, 20.0 mmol) was then added over 2 minutes, and the reaction mixture was stirred at room temperature for 18 hrs. The reaction mixture was partitioned between ether (200 mL) and water (100 mL). The organic layer was washed with saturated aqueous solution of sodium bicarbonate (150 mL), washed with water (100 mL), washed with brine (100 mL), and dried over anhydrous sodium sulfate. Concentration afforded a light yellow liquid that was chromatographed on a 5×20 cm silica gel column eluting with a 0-5% EtOAc/Hex gradient. The pure fractions were concentrated to afford (E,Z)-ethyl 2-bromohex-2-enoate (3.61 g, 16.3 mmol, 82% yield) as a colorless liquid. HPLC retention time=1.81 minutes (PHENOMENEX® Luna 4.6×30 mm S-5 ODS column) eluting with 10-90% aqueous methanol+0.1% TFA over a 2 minute gradient. MS: (M+H)=221/223.08. [Note: The product is approximately a 3:1 mixture of E/Z isomers, and was used in the next step without further purification.]

6-B. Ethyl 4-propyl-3-(pyridin-2-yl)isoxazole-5-carboxylate

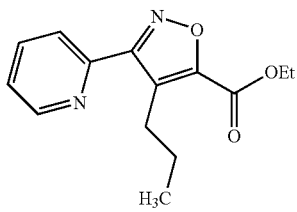

(6-B)

To a light orange, homogeneous mixture of (Z)—N-hydroxypicolinimidoyl chloride (0.637 g, 4.07 mmol) and ethyl 2-bromohex-2-enoate (0.900 g, 4.07 mmol) in dichloromethane (17 mL) and N,N-dimethylformamide (1 mL) at room temperature was added triethylamine (1.70 mL, 12.2 mmol) slowly over 5 min. The homogeneous reaction mixture was stirred at room temperature over the weekend. The solvent was removed under reduced pressure, and the residue was diluted with ether (100 mL), washed with water (3×75 mL), washed with a saturated aqueous solution of lithium chloride (1×75 mL), and dried over anhydrous sodium sulfate. Concentration under reduced pressure followed by trituration with hexane, with sonication, afforded a reddish solid and the hexane filtrate containing the desired product and remaining ethyl 2-bromohex-2-enoate. Concentration under reduced pressure followed by purification by flash silica gel chromatography using a mixture of ethyl acetate and hexane (0:100-0.5:99.5-1:99) afforded ethyl 4-propyl-3-(pyridin-2-yl)isoxazole-5-carboxylate (0.015 g, 0.058 mmol, 1.5% yield) as a white solid. The compound had an HPLC ret. time=2.61 min.—Column: CHROMOLITH® SpeedROD 4.6×50 mm (4 min.); Solvent A=10% MeOH, 90% $H_2O$, 0.1% TFA; Solvent B=90% MeOH, 10% H$_2$O, 0.1% TFA. LC/MS M$^{+1}$=261.0. $^1$H NMR (500 MHz, CDCl$_3$) δ ppm 0.92 (t, J=7.42 Hz, 3H), 1.45 (t, J=7.15 Hz, 3H), 1.55-1.64 (m, 2H), 3.11-3.17 (m, 2H), 4.47 (q, J=7.15 Hz, 2H), 7.37 (dd, J=7.70, 4.95 Hz, 1H), 7.81 (td, J=7.70, 2.20 Hz, 1H), 7.98 (d, J=7.70 Hz, 1H), and 8.72 (d, 1H).

6-C. 4-Propyl-3-(pyridin-2-yl)isoxazole-5-carboxylic acid

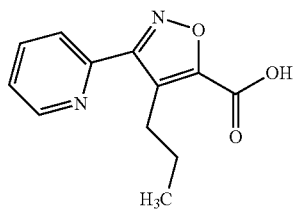

(6-C)

A mixture of ethyl 4-propyl-3-(pyridin-2-yl)isoxazole-5-carboxylate (0.015 g, 0.058 mmol) and lithium hydroxide, monohydrate (2.418 mg, 0.058 mmol) in methanol (1.0 mL) and water (0.5 mL) was stirred at room temperature overnight. The reaction mixture was concentrated to dryness to give 4-propyl-3-(pyridin-2-yl)isoxazole-5-carboxylic acid, lithium salt (0.014 g, 0.059 mmol, 102% yield) as a pale yellow solid. The compound had an HPLC ret. time=1.70 min.—Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=232.8.

6. Preparation of 1-(4-(5-(4-propyl-3-(pyridin-2-yl)isoxazol-5-yl)-1,2,4-oxadiazol-3-yl)benzyl)azetidine-3-carboxylic acid A mixture of 4-propyl-3-(pyridin-2-yl)isoxazole-5-carboxylic acid, lithium salt (13.5 mg, 0.058 mmol), tert-butyl 1-(4-(N'-hydroxycarbamimidoyl)benzyl)azetidine-3-carboxylate, Int. 1 (7.8 mg, 0.058 mmol), HOBt (16.02 mg, 0.105 mmol), N1-((ethylimino)methylene)-N3,N3-dimethylpropane-1,3-diamine hydrochloride (26.1 mg, 0.136 mmol), and diisopropylethylamine (0.041 mL, 0.233 mmol) in acetonitrile (1 mL) was stirred at 80° C. for 2 h. The reaction mixture was concentrated, and the residue was diluted with ethyl acetate (3 mL), washed a saturated aqueous solution of sodium bicarbonate (1 mL), washed with water (1 mL), washed with brine (1 mL), and dried over anhydrous sodium sulfate. Concentration followed by purification by preparative HPLC afforded tert-butyl 1-(4-(5-(4-propyl-3-(pyridin-2-yl)isoxazol-5-yl)-1,2,4-oxadiazol-3-yl)benzyl)azetidine-3-carboxylate.

To a solution of tert-butyl 1-(4-(5-(4-propyl-3-(pyridin-2-yl)isoxazol-5-yl)-1,2,4-oxadiazol-3-yl)benzyl)azetidine-3-carboxylate in dichloromethane (0.5 mL) was added trifluoroacetic acid (0.5 mL). The reaction mixture was stirred for 30 min. at room temperature and then concentrated to afford 1-(4-(5-(4-propyl-5-phenylisoxazol-3-yl)-1,2,4-oxadiazol-3-yl)benzyl)azetidine-3-carboxylic acid, 2,2,2-trifluoroacetic acid salt. The compound had an HPLC retention time=7.35 min.—Column: Xbridge Ph 3.5 u 4.6×150 mm; Gradient time: 12 min, hold for 3 minutes; Flow rate=2 ml/min; Solvent A=5% MeCN—95% Water—0.05% TFA; Solvent B=95% MeCN—5% water—0.05% TFA; Start % B=10; Final % B=100. LC-MS: M$^{+1}$=446+. $^1$H NMR (500 MHz, MeOD) δ ppm 1.04 (t, 3H), 1.73-1.83 (m, 2H), 3.34-3.40 (m, 2H), 3.73 (t, J=8.25 Hz, 1H), 4.39 (d, J=7.42 Hz, 4H), 4.54 (s, 2H), 7.51 (ddd, J=6.74, 4.67, 2.06 Hz, 1H), 7.70 (d, J=8.25 Hz, 2H), 7.98-8.05 (m, 2H), 8.30 (d, J=8.25 Hz, 2H), and 8.78 (d, J=4.40 Hz, 1H).

Example 7

1-(4-(5-(4-(Methoxycarbonyl)-3-(pyridin-2-yl)isoxazol-5-yl)-1,2,4-oxadiazol-3-yl)benzyl)azetidine-3-carboxylic acid

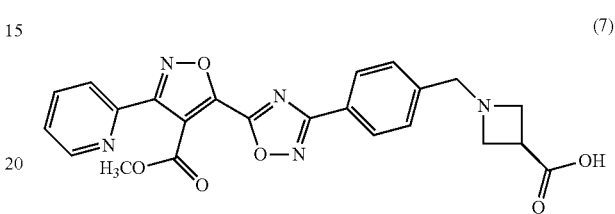

(7)

7-A. Dimethyl 3-(pyridin-2-yl)isoxazole-4,5-dicarboxylate

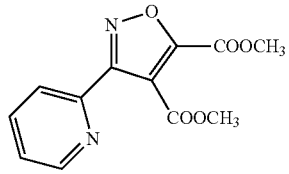

(7-A)

To a solution of (E,Z)—N-hydroxypicolinimidoyl chloride (313 mg, 2 mmol) and dimethyl but-2-ynedioate (0.249 mL, 2.000 mmol) in ether (8 mL) at room temperature was added triethylamine (0.307 mL, 2.200 mmol) dropwise over 5 min. The reaction mixture was stirred at room temperature for 2 h. The reaction mixture was concentrated to an oil that was chromatographed on a 24 gm Isco silica gel cartridge, eluting with a 0-20% EtOAc/Hex gradient. The pure fractions were concentrated to afford dimethyl 3-(pyridin-2-yl)isoxazole-4,5-dicarboxylate (416 mg, 1.59 mmol, 79% yield) as a colorless oil. HPLC retention time=2.35 minutes (YMC-Combi 4.6×50 mm S-5 ODS column) eluting with 10-90% aqueous methanol+0.2% phosphoric acid over a 4 minute gradient. MS: (M+H)=263.18. $^1$H NMR (400 MHz, CDCl$_3$) δ ppm 3.98 (s, 3H), 4.01 (s, 3H), 7.38 (ddd, J=7.6, 4.8, 1.1 Hz, 1H), 7.83 (td, J=7.8, 1.8 Hz, 1H), 8.08 (d, J=7.8 Hz, 1H), and 8.65 (d, J=4.8 Hz, 1H). [The product was contaminated with an unknown impurity of approximately 17% as estimated by analysis of HPLC, LCMS and NMR data. This material was used in the next step without further purification.]

7-B. 4-(Methoxycarbonyl)-3-(pyridin-2-yl)isoxazole-5-carboxylic acid

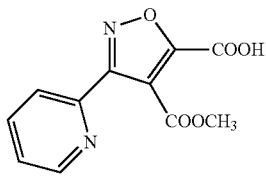

(7-B)

To a solution of dimethyl 3-(pyridin-2-yl)isoxazole-4,5-dicarboxylate (410 mg, 1.56 mmol) in methanol (12 mL) and water (3 mL) at room temperature was added lithium hydroxide, monohydrate (49.2 mg, 1.17 mmol), and the reaction mixture was allowed to stir at room temperature for 1.5 h. At this time, the methanol was removed under reduced pressure, and the remaining aqueous residue was diluted to ~10 ml with water. The aqueous layer was washed with ethyl acetate (20 mL). The pH of the aqueous phase was then adjusted to ~3-4 with 1N aqueous hydrochloric acid, and the aqueous layer was extracted with ethyl acetate (2×30 ml). The combined organic layers were dried (sodium sulfate/magnesium sulfate) and concentrated to afford 60 mg of product. The aqueous layer was saturated with anhydrous sodium sulfate and was then extracted with ethyl acetate (3×30 mL). After drying (magnesium sulfate) and concentration, an additional 20 mg of the product was obtained. All material was combined to give 4-(methoxycarbonyl)-3-(pyridin-2-yl)isoxazole-5-carboxylic acid (80 mg, 0.322 mmol, 21% yield) as a light tan solid. HPLC retention time=1.17 minutes (YMC-Combi 4.6× 50 mm S-5 ODS column) eluting with 10-90% aqueous methanol+0.2% phosphoric acid over a 4 minute gradient. MS: (M+H)=249.12. $^1$H NMR (400 MHz, CDCl$_3$) δ ppm 3.79 (s, 3H), 7.33 (brs, 1H), 7.75 (m, 1H), 7.81 (m, 1H), and 8.63 (brs, 1H).

7-C. Methyl 5-(3-(4-((3-(tert-butoxycarbonyl)azetidin-1-yl)methyl)phenyl)-1,2,4-oxadiazol-5-yl)-3-(pyridin-2-yl)isoxazole-4-carboxylate

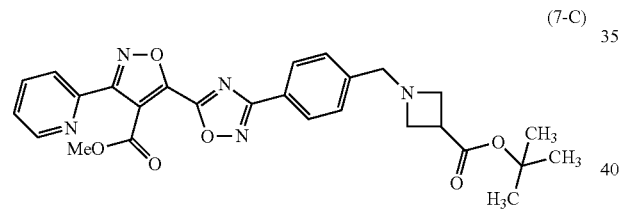

(7-C)

To a mixture of 4-(methoxycarbonyl)-3-(pyridin-2-yl)isoxazole-5-carboxylic acid (79 mg, 0.318 mmol), tert-butyl 1-(4-(N'-hydroxycarbamimidoyl)benzyl)azetidine-3-carboxylate, Int. 1 (97 mg, 0.318 mmol), and BOP—Cl (97 mg, 0.382 mmol) in dimethylformamide (1.5 mL) at room temperature was added triethylamine (0.133 mL, 0.955 mmol). The reaction mixture was allowed to stir at room temperature overnight. Some uncyclized material remained, so stirring was continued for an additional 24 hrs. At this time, the reaction mixture was partitioned between ethyl acetate (30 mL) and a saturated aqueous solution of sodium bicarbonate (30 mL). The organic layer was washed with water (2×30 mL), washed with brine (30 mL), and dried over anhydrous magnesium sulfate. Concentration afforded a brown oil that was chromatographed on a 4 gm Isco silica gel cartridge, eluting with a 0-70% EtOAc/Hex gradient. The essentially pure fractions containing product were concentrated to afford methyl 5-(3-(4-((3-(tert-butoxycarbonyl)azetidin-1-yl)methyl)phenyl)-1,2,4-oxadiazol-5-yl)-3-(pyridin-2-yl)isoxazole-4-carboxylate (80 mg, 0.155 mmol, 48.6% yield) as a light purple solid. HPLC retention time=2.91 minutes (YMC-Combi 4.6×50 mm S-5 ODS column) eluting with 10-90% aqueous methanol+0.2% phosphoric acid over a 4 minute gradient. MS: (M+H)=518.20.

7. Preparation of 1-(4-(5-(4-(methoxycarbonyl)-3-(pyridin-2-yl)isoxazol-5-yl)-1,2,4-oxadiazol-3-yl)benzyl)azetidine-3-carboxylic acid A solution of methyl 5-(3-(4-((3-(tert-butoxycarbonyl)azetidin-1-yl)methyl)phenyl)-1,2,4-oxadiazol-5-yl)-3-(pyridin-2-yl)isoxazole-4-carboxylate (79 mg, 0.153 mmol) in trifluoroacetic acid (2 mL) was allowed to stand at room temperature for 1 h. The volatiles were removed under reduced pressure, and the residue was suspended in water. The pH was adjusted to ~4 with a 1N aqueous solution of sodium hydroxide, and the resulting suspension was allowed to stir briskly overnight. Filtration and drying afforded 1-(4-(5-(4-(methoxycarbonyl)-3-(pyridin-2-yl)isoxazol-5-yl)-1,2,4-oxadiazol-3-yl)benzyl)azetidine-3-carboxylic acid (65 mg, 0.141 mmol, 92% yield) as a slightly off-white powder. HPLC retention time=2.51 minutes (YMC-Combi 4.6×50 mm S-5 ODS column) eluting with 10-90% aqueous methanol+0.2% phosphoric acid over a 4 minute gradient. MS: (M+H)=462.18. $^1$H NMR (500 MHz, MeOD) δ ppm 3.61-3.68 (m, 1H), 3.98 (s, 3H), 4.30-4.37 (m, 4H), 4.50 (s, 2H), 7.53-7.56 (m, 1H), 7.68 (d, J=8.3 Hz, 2H), 7.98-8.02 (m, 1H), 8.09 (d, J=7.7 Hz, 1H), 8.26 (d, J=8.8 Hz, 2H), and 8.69 (d, J=4.4 Hz, 1H).

Example 8

1-(4-(5-(3-(Pyridin-2-yl)isoxazol-5-yl))-1,2,4-oxadiazol-3-yl)benzyl)azetidine-3-carboxylic acid

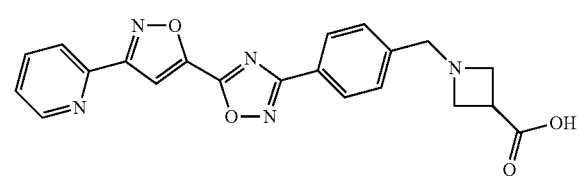

(8)

Example 8 was prepared using the general procedures described hereinabove. Example 8 was prepared starting with 2-B. HPLC retention time=2.33 min. (YMC S5 COMBISCREEN® 4.6×50 mm column over a 4 min. gradient); Solvent A=10% MeOH, 90% H$_2$O, 0.1% TFA; Solvent B=90% MeOH, 10% H$_2$O, 0.1% TFA; MW 403.4; MS (M$^{+1}$=404.1.

Comparative Compound A (Comp. A)

1-(4-(5-(4-Phenyl-5-(trifluoromethyl)thiophen-2-yl)-1,2,4-oxadiazol-3-yl)benzyl)azetidine-3-carboxylic acid A comparative compound (Comp. A) was prepared for evaluation. This compound is Example 54 from WO 2003/062252 which has also been described in Hale et al., *J. Med. Chem.*, 6662 (2004).

(Comp. A)

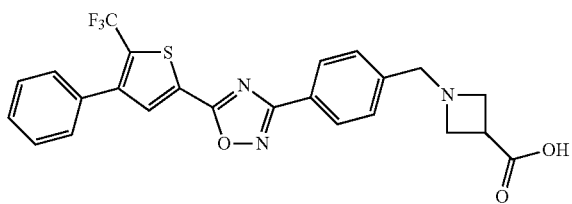

Comp. A-1. (Z)-tert-Butyl 1-(4-(N'-(4-phenyl-5-(trifluoromethyl)thiophene-2-carbonyloxy)-carbamimidoyl)benzyl)azetidine-3-carboxylate (Comp. A-1)

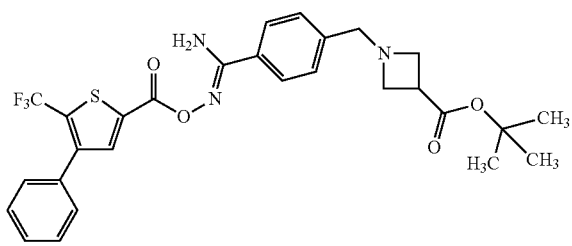

A mixture of 4-phenyl-5-(trifluoromethyl)thiophene-2-carboxylic acid (408 mg, 1.50 mmol), (Z)-tert-butyl 1-(4-(N'-hydroxycarbamimidoyl)benzyl)azetidine-3-carboxylate, Int. 1 (458 mg, 1.50 mmol), HOBT (345 mg, 2.250 mmol), Hunig's Base (1.05 mL, 6.00 mmol), and EDC (431 mg, 2.25 mmol) in N,N-dimethylformamide (7.5 mL) was stirred at room temperature for 18 h. The reaction mixture was partitioned between ethyl acetate (120 mL) and a saturated aqueous solution of sodium bicarbonate (60 mL). The organic layer was washed with water (2×120 mL), washed with brine (120 mL), and dried over anhydrous magnesium sulfate. Concentration under reduced pressure afforded ten-butyl 1-(4-(N'-(4-phenyl-5-(trifluoromethyl)thiophene-2-carbonyloxy)carbamimidoyl)benzyl)azetidine-3-carboxylate (744 mg, 1.33 mmol, 89% yield) as a light peach colored solid that was used in the next step without further purification. HPLC: ret. time=3.26 minutes (YMC Combi S-5 4.6×50 mm ODS column) eluting with 10-90% aqueous methanol+0.2% phosphoric acid over a 4 minute gradient. MS: (M+H)=560.25.

Comp. A-2. tert-Butyl 1-(4-(5-(4-phenyl-5-(trifluoromethyl)thiophen-2-yl)-1,2,4-oxadiazol-3-yl)benzyl)azetidine-3-carboxylate (Comp. A-2)

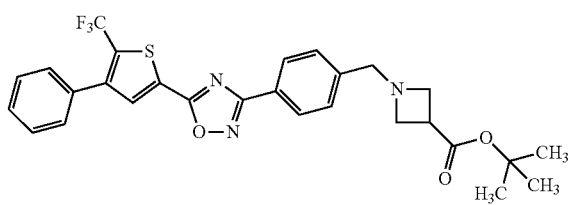

To a solution of tert-butyl 1-(4-(N'-(4-phenyl-5-(trifluoromethyl)thiophene-2-carbonyloxy)carbamimidoyl)benzyl)azetidine-3-carboxylate (744 mg, 1.33 mmol) in acetonitrile (30 mL) was added a 1M solution of TBAF in tetrahydrofuran (3.99 mL, 3.99 mmol), and the reaction mixture was allowed to stir at room temperature for 3 days. The volatiles were removed under reduced pressure, and the residue was chromatographed on a 5×12 cm silica gel column, eluting with a 0-50% EtOAc/Hex gradient. The essentially pure fractions containing product were concentrated to afford tert-butyl 1-(4-(5-(4-phenyl-5-(trifluoromethyl)thiophen-2-yl)-1,2,4-oxadiazol-3-yl)benzyl)azetidine-3-carboxylate (521 mg, 0.962 mmol, 72.4% yield) as a colorless solid. HPLC ret. time=3.63 min. (YMC Combi S-5 4.6×50 mm ODS column) eluting with 10-90% aqueous methanol+0.2% phosphoric acid over a 4 minute gradient. MS: (M+H)=542.22. $^1$H NMR (500 MHz, $CDCL_3$) δ ppm 1.46 (s, 9H), 3.25-3.31 (m, 3H), 3.52-3.58 (m, 2H), 3.69 (s, 2H), 7.43 (d, J=8.25 Hz, 2H), 7.47 (m, 5H), 7.91 (s, d, J=1.65 Hz, 1H), and 8.09 (d, J=8.25 Hz, 2H).

Comp. A. Preparation of 1-(4-(5-(4-phenyl-5-(trifluoromethyl)thiophen-2-yl)-1,2,4-oxadiazol-3-yl)benzyl)-azetidine-3-carboxylic acid A solution of tert-butyl 1-(4-(5-(4-phenyl-5-(trifluoromethyl)thiophen-2-yl)-1,2,4-oxadiazol-3-yl)benzyl)azetidine-3-carboxylate (518 mg, 0.956 mmol) in trifluoroacetic acid (15 mL) was allowed to stand at room temperature for 1.5 h. The volatiles were removed under reduced pressure, and the residue was co-evaporated from ethyl acetate/hexanes. (2×10 mL). The residue was suspended in water (10 mL) and the pH was adjusted to ~11 with 1N aqueous sodium hydroxide. To this solution was added sufficient 1N aqueous hydrochloric acid to adjust the pH ~4.5. The resulting suspension was stirred at room temperature overnight. The white suspension was filtered through a medium porosity sintered glass filter, and the filter cake was washed thoroughly with water. The solid was dried, the white powder was suspended in methanol, and the suspension was sonicated until it was uniform. The methanol was removed under reduced pressure, and the procedure was repeated twice more to afford a white solid that was stirred as a suspension in methanol (~30 mL) overnight. Vacuum filtration and drying afforded 1-(4-(5-(4-phenyl-5-(trifluoromethyl)thiophen-2-yl)-1,2,4-oxadiazol-3-yl)benzyl)-azetidine-3-carboxylic acid (345 mg, 0.707 mmol, 74% yield) as a white powder. HPLC ret. time=3.45 min. (YMC Combi S-5 4.6×50 mm ODS column) eluting with 10-90% aqueous methanol+0.2% phosphoric acid over a 4 minute gradient. MS: (M+H)=486.12. $^1$H NMR (400 MHz, DMSO-$d_6$) δ ppm 3.23 (s, 3H), 3.39-3.45 (m, 2H), 3.64 (s, 2H), 7.50 (d, J=8.28 Hz, 2H), 7.58 (m, 5H), 8.02 (d, J=8.28 Hz, 2H), and 8.26 (d, J=1.25 Hz, 1H). Elemental Analysis: Calc. for $C_{24}H_{18}N_3O_3SF_3 \cdot 0.1H_2O$: C, 59.22; H, 3.76; N, 8.63; S, 6.59; F, 11.71. Found: $C_{24}H_{18}N_3O_3SF_3 \cdot 0.1H_2O$: C, 59.06; H, 3.45; N, 8.60; S, 6.61; F, 11.42; KF (Found)=0.25% water.

Biological Assays $S1P_1$ Binding Assay

Membranes were prepared from CHO cells expressing human $S1P_1$. Cells were dissociated in buffer containing 20 mM HEPES, pH 7.5, 50 mM NaCl, 2 mM EDTA and Protease Inhibitor cocktail (Roche), and disrupted on ice using the Polytron homogenizer. The homogenate was centrifuged at 20,000 rpm (48,000 g) and the supernatant was discarded. The membrane pellets were resuspended in buffer containing 50 mM HEPES, pH 7.5, 100 mM NaCl, 1 mM $MgCl_2$, 2 mM EDTA and stored in aliquots at −80° C. after protein concentration determination.

Membranes (2 mg/well) and 0.03 nM final concentration of $^{33}P$—S1P ligand (1 mCi/ml, American Radiolabeled Chemicals) were added to the compound plates. Binding was performed for 60 min at room temperature, terminated by collecting the membranes onto GF/B filter plates, and radioactivity was measured by TOPCOUNT®. The competition data of the test compounds over a range of concentrations was plotted as percentage inhibition of radioligand specific binding. The $IC_{50}$ is defined as the concentration of competing ligand needed to reduce specific binding by 50%.

Compounds of the present invention and Comparative Compound A were tested in the $S1P_1$ binding assay described hereinabove and the results rounded to two digits, shown in Table A were obtained. In some instances, the value is an average of multiple experiments where N is the number of experiments conducted that provided satisfactory dose response curves. When more than one batch of an example was tested, the value presented is from the batch which allowed a comparison of GTPγS $S1P_1$ and GTPγS $S1P_3$ in Method A (Data shown in Table B). Data was not averaged across different batches of an example compound.

TABLE A

| Ex. | $S1P_1$ Binding $IC_{50}$ (nM) | N |
| --- | --- | --- |
| 1 | 0.21 | 1 |
| 2 | 0.39 | 1 |
| 3 | 0.021 | 2 |
| 4 | 0.18 | 3 |
| 5 | 0.051 | 1 |
| 6 | 0.019 | 1 |
| 7 | 0.53 | 1 |
| 8 | 6.5 | 1 |
| Comp. A | 2.5 | 1 |

Method A: Receptor [35S] GTPγS Binding Assays

Compounds were loaded in a 384 Falcon v-bottom plate (0.5 μl/well in a 3-fold dilution). Membranes prepared from $S1P_1$/CHO cells or EDG3-Gal5-bla HEK293T cells were added to the compound plate (40 μl/well, final protein 3 μg/well) with MULTIDROP®. [$^{35}$S]GTP (1250 Ci/mmol, Perkin Elmer) was diluted in assay buffer: 20 mM HEPES, pH 7.5, 10 mM $MgCl_2$, 150 mM NaCl, 1 mM EGTA, 1 mM DTT, 10 μM GDP, 0.1% fatty acid free BSA, and 10 μg/ml Saponin to 0.4 nM. 40 μl of the [$^{35}$S] GTP solution was added to the compound plate with a final concentration of 0.2 nM. The reaction was kept at room temperature for 45 min. At the end of incubation, all the mixtures in the compound plate were transferred to a 384 well FB filter plates via GPCR robot system. The filter plate was washed with water 4 times by using the modified manifold Embla plate washer and dried at 60° C. for 45 min. 30 μA of MicroScint 20 scintillation fluid was added to each well for counting at Packard TOP-COUNT®. $EC_{50}$ is defined as the agonist concentration that corresponds to 50% of the Ymax (maximal response) obtained for each individual compound tested.

Method B: Receptor [35S] GTPγS SPA Binding Assays

Membranes prepared from $S1P_1$ or $S1P_3$ transfected CHO cells (2 mg protein) were incubated in 96-well white plates (CORNING® 3693) with test compounds diluted in DMSO, in 50 μl of reaction mixture containing 7.5 μl WGA-PVT beads (20 mg/ml), and 5 μM GDP, 20 mM HEPES pH 7.4, 100 mM NaCl, 1 mM EDTA, 5 mM $MgCl_2$, 10 μg/ml saponin, 0.1% BSA, and 1 μM leupeptin. The assay was initiated with the addition of 25 μA of 0.2 nM [$^{35}$S]-GTPγS (1250 Ci/mmol; NEN) in assay buffer. After 90 min incubation at room temperature, spin the plate at 1000 rpm for 5 min. The bound radionuclides were measured at TOPCOUNT®, expressed as % response relative to S1P (1 μM) activation. Data was analyzed using the four parameter logistic equation in Excel. The four parameters in the equation, $Y=A+((B-A)/(1+((EC_{50}/X)^D)))$, are described as following: A is the Y value (agonist activity) at the bottom plateau; B is the Y value at the top plateau; $EC_{50}$ is the X value (agonist concentration) when the response is halfway between bottom and top; D is Hill coefficient. Curves were not generated for compounds having Ymax values were below 50%.

Compounds of the present invention and Comparative Compound A were tested in the Receptor [35S] GTPγS Binding Assays (Method A) and Receptor [35S] GTPγS SPA Binding Assays (Method B) described hereinabove and the results rounded to two digits, shown in Table B were obtained. In some instances, the value is an average of multiple experiments where N is the number of experiments conducted that provided satisfactory dose response curves. When more than one batch of an example was tested, the value presented is from a batch which allowed a comparison of GTPγS $S1P_1$ and GTPγS $S1P_3$ in which the most number of experiments were performed. Preferably, the same batch was examined in Method A and Method B. Data was not averaged across different batches of an example compound.

TABLE B

| | Method A | | | | Method B | | | |
| --- | --- | --- | --- | --- | --- | --- | --- | --- |
| Ex. | GTPγS $S1P_1$ $EC_{50}$ (nM) | N | GTPγS $S1P_3$ $EC_{50}$ (nM) | N | GTPγS $S1P_1$ $EC_{50}$ (nM) | N | GTPγS $S1P_3$ $EC_{50}$ (nM) | N |
| 1 | 1.4 | 1 | NC | 0 | 0.17 | 11 | 6,200 | 8 |
| 2 | 4.5 | 1 | ND | 0 | 0.34 | 10 | 4,400 | 5 |
| 3 | 0.82 | 1 | 2,100 | 1 | 0.65 | 3 | 280 | 3 |
| 4 | 39 | 2 | 7,000 | 1 | 1.0 | 1 | ND | 0 |
| 5 | 3.7 | 1 | 1,900 | 1 | 0.61 | 6 | ND | 0 |
| 6 | ND | 0 | ND | 0 | 0.082 | 9 | 430 | 3 |
| 7 | 3.3 | 1 | 19,000 | 2 | ND | 0 | ND | 0 |
| 8 | 450 | 2 | 2,300 | 1 | 68 | 1 | ND | 0 |
| Comp. A | 84 | 1 | 97 | 1 | 0.25 | 10 | 20 | 3 |

ND = not determined.

NC = a satisfactory dose response curve was not obtained.

The ratios of the GTPγS S1P$_3$ EC$_{50}$ values to the GTPγS S1P$_1$ EC$_{50}$ values, calculated from the data in Table B, are shown in Table C.

TABLE C

| Ex. | GTPγS S1P$_3$/S1P$_1$ (Method A) | GTPγS S1P$_3$/S1P$_1$ (Method B) |
|---|---|---|
| 1 | ND | 37,000 |
| 2 | ND | 13,000 |
| 3 | 2,600 | 430 |
| 4 | 179 | ND |
| 5 | 513 | ND |
| 6 | ND | 5,200 |
| 7 | 5,800 | ND |
| 8 | 5.1 | ND |
| Comp. A | 1.2 | 78 |

In Table C, a larger value for the ratio of the GTPγS S1P$_3$ EC$_{50}$ value to the GTPγS S1P$_1$ EC$_{50}$ value indicates greater selectivity of S1P$_1$ activity over S1P$_3$ activity.

The compounds of the present invention, as exemplified by Examples 1 to 8, show the surprising advantage as agonists of S1P$_1$ and are selective over S1P$_3$, as compared to Comparative Compound A. Exemplified compounds of the invention reported in Table C had selectivity ratios in the range of 179 to 5,800, while in contrast, Comparative Compound A had a selectivity ratio of 1.2, as measured by Method A. Exemplified compounds of the invention reported in Table C had selectivity ratios in the range of 430 to 37,000, while in contrast, Comparative Compound A had a selectivity ratio of 78, as measured by Method B.

The compounds of the present invention possess activity as agonists of S1P$_1$ and are selective over S1P$_3$, and thus may be used in treating, preventing, or curing various S1P$_1$ receptor-related conditions while reducing or minimizing the side effects due to S1P$_3$ activity. The surprising selectivity of the compounds of the present invention indicate their potential use in treating, preventing, or curing autoimmune and inflammatory diseases such as multiple sclerosis, rheumatoid arthritis, inflammatory bowel disease, or psoriasis, while reducing or minimizing possible cardiovascular side effects such as bradycardia and hypertension. Other potential uses of the compounds of the present invention include minimizing or reducing rejection of transplanted organs, while reducing or minimizing side effects due to S1P$_3$ activity.

Blood Lymphocyte Reduction Assay (BLR) in Rodents

Lewis rats or BALB/c mice were dosed orally with test article (as a solution or suspension in the vehicle) or vehicle alone (polyethylene glycol 300, "PEG300"). Blood was drawn at 4 hr and 24 h by retro-orbital bleeding. Blood lymphocyte counts were determined on an ADVIA® 120 Hematology Analyzer (Siemens Healthcare Diagnostics). The results were measured as a reduction in the percentage of circulating lymphocytes as compared to the vehicle treated group at the 4 hr and 24 hr measurement. The results represent the average results of all animals within each treatment group (n=3-4).

A compound of the present invention was tested in the Blood Lymphocyte Reduction assay (BLR) described hereinabove and the results are shown in Table D for rats and Table E for mice.

TABLE D

| Dose (mg/kg) | Example 1 % reduction in lymphocytes at 4 hr. | Example 1 % reduction in lymphocytes at 24 hr. |
|---|---|---|
| 0.3 | 82% | 48% |
| 1.0 | 85% | 80% |

TABLE E

| Dose (mg/kg) | Example 1 % reduction in lymphocytes at 4 hr. | Example 1 % reduction in lymphocytes at 24 hr. |
|---|---|---|
| 0.008 | 13% | 8% |
| 0.04 | 67% | 39% |
| 0.2 | 82% | 74% |
| 1.0 | 83% | 77% |

Rat Adjuvant Induced Arthritis Assay (AA)

Male Lewis rats (150-175 g; Harlan, n=8 treatment group) were immunized at the base of the tail with 100 μl of 10 mg/ml freshly ground *Mycobacterium butyricum* (Difco Laboratories) in incomplete Freund's adjuvant (sigma). Animals were dosed once daily with the test article (as a solution or suspension in the vehicle) or vehicle alone (polyethylene glycol 300, "PEG300") starting from the day of immunization. The volumes of their hind paws were measured in a water displacement plethysmometer (Ugo Basile, Italy). The baseline paw measurements were taken before onset of the disease (between day 7 to day 10). The paw measurements were then taken three times a week until the end of the study on day 20. All procedures involving animals were reviewed and approved by the Institutional Animal Care Use Committee.

A compound of the present invention was tested in the Rat Adjuvant Induced Arthritis assay described hereinabove and the results are shown in Table F.

TABLE F

| Group | | Paw Swelling (mL) on Day 20 |
|---|---|---|
| Vehicle | Mean | 1.11 |
| | SD | 0.67 |
| Example 1 (0.03 mg/kg) | Mean | 1.48 |
| | SD | 0.92 |
| Example 1 (0.1 mg/kg) | Mean | 1.41 |
| | SD | 0.50 |
| Example 1 (0.5 mg/kg) | Mean | 0.72 |
| | SD | 0.79 |
| Example 1 (3.0 mg/kg) | Mean | 0.07 |
| | SD | 0.12 |

In the rat adjuvant-induced arthritis model, an animal model for rheumatoid arthritis, Example 1 inhibits disease progression as measured by paw swelling in the Lewis rat using a prophylactic oral dosing regiment.

What is claimed is:

1. A compound of Formula (I):

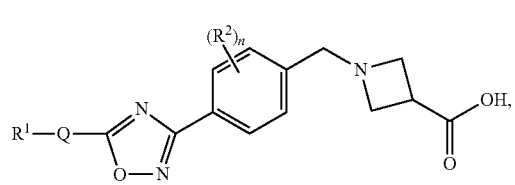

or a pharmaceutically acceptable salt thereof, wherein:

Q is

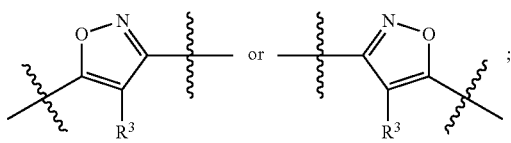

n is zero or an integer selected from 1 through 4;

$R^1$ is cycloalkyl, heteroaryl, or heterocyclyl, each optionally substituted with one to five substituents independently selected from $C_1$ to $C_6$ alkyl, $C_1$ to $C_4$ haloalkyl, —$OR^4$, and/or halogen;

each $R^2$ is independently selected from hydrogen, $C_1$ to $C_6$ alkyl, $C_1$ to $C_4$ haloalkyl, —$OR^4$, and/or halogen;

$R^3$ is hydrogen, alkyl, cycloalkyl, haloalkyl, —$C(O)OR^5$, or —$C(O)NR_aR_b$;

each $R^4$ is independently selected from $C_1$ to $C_6$ alkyl, $C_1$ to $C_4$ haloalkyl, and/or benzyl;

$R^5$ is alkyl or benzyl; and $R_a$ and $R_b$ are independently selected from hydrogen, alkyl, haloalkyl, and/or benzyl.

2. The compound of claim 1 or a pharmaceutically acceptable salt thereof, wherein $R^1$ is $C_3$ to $C_8$ cycloalkyl optionally substituted with one to five substituents independently selected from $C_1$ to $C_6$ alkyl, $C_1$ to $C_4$ haloalkyl, —$OR^4$, and/or halogen.

3. The compound of claim 1 or a pharmaceutically acceptable salt thereof, wherein $R^1$ is 1- to 2-ring heterocyclyl having 1 to 4 heteroatoms independently selected from O, N, and/or S, optionally substituted with one to five substituents independently selected from $C_1$ to $C_6$ alkyl, $C_1$ to $C_4$ haloalkyl, —$OR^4$, and/or halogen.

4. The compound of claim 1 or a pharmaceutically acceptable salt thereof, wherein $R^1$ is 1- to 2-ring heteroaryl having 1 to 4 heteroatoms independently selected from O, N, and/or S, optionally substituted with one to five substituents independently selected from $C_1$ to $C_6$ alkyl, $C_1$ to $C_4$ haloalkyl, —$OR^4$, and/or halogen.

5. The compound of claim 4 wherein said heteroaryl is a 1-ring heteroaryl, optionally substituted with one to five substituents independently selected from $C_1$ to $C_6$ alkyl, $C_1$ to $C_4$ haloalkyl, —$OR^4$, and/or halogen.

6. The compound according to claim 5 or a pharmaceutically acceptable salt thereof, having formula (Id):

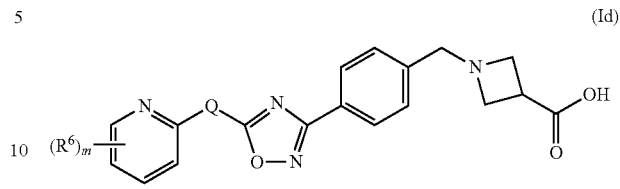

wherein:

m is zero or an integer selected from 1 through 4;

each $R^6$ is independently selected from $C_1$ to $C_6$ alkyl, $C_1$ to $C_4$ haloalkyl, halogen, and/or —$OR^4$;

each $R^4$ is independently $C_1$ to $C_4$ alkyl;

$R^3$ is $C_1$ to $C_6$ alkyl, $C_1$ to $C_4$ haloalkyl, or —$C(O)OR^5$; and $R^5$ is $C_1$ to $C_4$ alkyl.

7. The compound of claim 6 or a pharmaceutically acceptable salt thereof, wherein:

m is 0; and $R^3$ is hydrogen, ethyl, 1-propyl, 2-propyl, —$CF_3$, or —$C(O)OCH_3$.

8. The compound of claim 1 or a pharmaceutically acceptable salt thereof, selected from the group consisting of:

1-(4-(5-(3-(pyridin-2-yl)-4-(trifluoromethyl)isoxazol-5-yl)-1,2,4-oxadiazol-3-yl)benzyl)azetidine-3-carboxylic acid;

1-(4-(5-(5-(pyridin-2-yl)-4-(trifluoromethyl)isoxazol-3-yl)-1,2,4-oxadiazol-3-yl)benzyl)azetidine-3-carboxylic acid;

1-(4-(5-(4-propyl-5-(pyridin-2-yl)isoxazol-3-yl)-1,2,4-oxadiazol-3-yl)benzyl)azetidine-3-carboxylic acid;

1-(4-(5-(4-isopropyl-5-(pyridin-2-yl)isoxazol-3-yl)-1,2,4-oxadiazol-3-yl)benzyl)azetidine-3-carboxylic acid;

1-(4-(5-(4-ethyl-5-(pyridin-2-yl)isoxazol-3-yl)-1,2,4-oxadiazol-3-yl)benzyl)azetidine-3-carboxylic acid;

1-(4-(5-(4-Propyl-3-(pyridin-2-yl)isoxazol-5-yl)-1,2,4-oxadiazol-3-yl)benzyl)-azetidine-3-carboxylic acid;

1-(4-(5-(4-(methoxycarbonyl)-3-(pyridin-2-yl)isoxazol-5-yl)-1,2,4-oxadiazol-3-yl)benzyl)azetidine-3-carboxylic acid; and 1-(4-(5-(3-(pyridin-2-yl)isoxazol-5-yl))-1,2,4-oxadiazol-3-yl)benzyl)azetidine-3-carboxylic acid.

9. The compound of claim 1, wherein said pharmaceutically acceptable salt is a 2,2,2-trifluoroacetic acid salt.

10. A composition comprising a compound according to claim 1 or a pharmaceutically acceptable salt thereof, and a pharmaceutically acceptable carrier.

11. A method of treating a disease or disorder associated with the activity of G protein-coupled receptor $S1P_1$, the method comprising administering to a mammalian patient a compound according to claim 1 or a pharmaceutically acceptable salt thereof, wherein said disease or disorder is selected from multiple sclerosis, rheumatoid arthritis, inflammatory bowel disease, and psoriasis.

12. A method of treating an autoimmune disease or chronic inflammatory disease, the method comprising administering to a mammalian patient a compound according to claim 1 or a pharmaceutically acceptable salt thereof, wherein said autoimmune disease or chronic inflammatory disease is selected from multiple sclerosis, rheumatoid arthritis, inflammatory bowel disease, and psoriasis.

* * * * *

UNITED STATES PATENT AND TRADEMARK OFFICE
CERTIFICATE OF CORRECTION

PATENT NO. : 8,404,672 B2
APPLICATION NO. : 13/145721
DATED : March 26, 2013
INVENTOR(S) : William Pitts et al.

Page 1 of 1

It is certified that error appears in the above-identified patent and that said Letters Patent is hereby corrected as shown below:

Title Page, Col. 1, (73) Assignee,

Delete "Meyers" and insert -- Myers --, therefor.

In the Claims:

In Claim 3, col. 67, line 49, delete "0," and insert -- O, --, therefor.

In Claim 4, col. 67, line 55, delete "0," and insert -- O, --, therefor.

Signed and Sealed this
Fifth Day of November, 2013

Teresa Stanek Rea
*Deputy Director of the United States Patent and Trademark Office*